(12) United States Patent
Bardy et al.

(10) Patent No.: US 9,408,551 B2
(45) Date of Patent: Aug. 9, 2016

(54) SYSTEM AND METHOD FOR FACILITATING DIAGNOSIS OF CARDIAC RHYTHM DISORDERS WITH THE AID OF A DIGITAL COMPUTER

(71) Applicant: Bardy Diagnostics, Inc., Vashon, WA (US)

(72) Inventors: Gust H. Bardy, Carnation, WA (US); Ezra M. Dreisbach, Vashon, WA (US)

(73) Assignee: BARDY DIAGNOSTICS, INC., Vashon, WA (US)

( * ) Notice: Subject to any disclaimer, the term of this patent is extended or adjusted under 35 U.S.C. 154(b) by 0 days.

(21) Appl. No.: 15/066,883

(22) Filed: Mar. 10, 2016

(65) Prior Publication Data

US 2016/0192853 A1    Jul. 7, 2016

Related U.S. Application Data

(63) Continuation-in-part of application No. 14/997,416, filed on Jan. 15, 2016, now Pat. No. 9,345,414, which is a continuation-in-part of application No. 14/614,265, filed on Feb. 4, 2015, which is a
(Continued)

(51) Int. Cl.
*A61B 5/0432* (2006.01)
*A61B 5/0456* (2006.01)
(Continued)

(52) U.S. Cl.
CPC ............... *A61B 5/0456* (2013.01); *A61B 5/044* (2013.01); *A61B 5/04017* (2013.01); *A61B 5/0432* (2013.01); *A61B 5/04085* (2013.01); *A61B 5/6823* (2013.01)

(58) Field of Classification Search
CPC combination set(s) only.
See application file for complete search history.

(56) References Cited

U.S. PATENT DOCUMENTS 3,215,136 A    11/1965    Holter et al.
3,699,948 A    10/1972    Ota et al.
(Continued)

FOREIGN PATENT DOCUMENTS

DE    19955211    5/2001
EP    1859833    11/2007
(Continued)

OTHER PUBLICATIONS

US 6,527,714, 03/2003, Bardy (withdrawn).
(Continued)

*Primary Examiner* — Kennedy Schaetzle
(74) *Attorney, Agent, or Firm* — Patrick J. S. Inouye; Krista A. Wittman

(57) ABSTRACT

R-R interval data is presented in a format that includes relevant near field and far field ECG data. The near field view provides a "pinpoint" classical view at classical recording speed. The far field view that provides an "intermediate" lower resolution, pre- and post-event view. Both ECG data views are temporally keyed to the extended duration R-R interval data that is scaled non-linearly to maximize the visual differentiation for frequently-occurring heart rate ranges. All three views are presented simultaneously. The durations of the pinpoint view, the intermediate view, and the R-R interval plot are flexible and adjustable. Diagnostically relevant cardiac events can be identified and located to allow pre- and post-event heart rhythm data. The pinpoint "snapshot" and intermediate views of ECG data with the extended term R-R interval data comparatively depicts heart rate context and patterns of behavior prior to and after a clinically meaningful arrhythmia or patient concern.

21 Claims, 9 Drawing Sheets

Related U.S. Application Data continuation-in-part of application No. 14/488,230, filed on Sep. 16, 2014, which is a continuation-in-part of application No. 14/080,725, filed on Nov. 14, 2013.

(60) Provisional application No. 62/132,497, filed on Mar. 12, 2015.

(51) Int. Cl.
  *A61B 5/04* (2006.01)
  *A61B 5/00* (2006.01)
  *A61B 5/0408* (2006.01)
  *A61B 5/044* (2006.01)

(56) References Cited

U.S. PATENT DOCUMENTS

| | | | |
|---|---|---|---|
| 3,893,453 A * | 7/1975 | Goldberg | A61B 5/0432 346/138 |
| 4,123,785 A | 10/1978 | Cherry et al. | |
| 4,328,814 A | 5/1982 | Arkans | |
| 4,532,934 A | 8/1985 | Kelen | |
| 4,550,502 A | 11/1985 | Grayzel | |
| 4,716,903 A | 1/1988 | Hansen | |
| 4,809,705 A | 3/1989 | Ascher | |
| 4,915,656 A | 4/1990 | Alferness | |
| 5,025,794 A | 6/1991 | Albert et al. | |
| 5,168,876 A | 12/1992 | Quedens et al. | |
| 5,215,098 A | 6/1993 | Steinhaus | |
| D341,423 S | 11/1993 | Bible | |
| 5,341,806 A | 8/1994 | Gadsby et al. | |
| 5,355,891 A * | 10/1994 | Wateridge | A61B 5/04325 600/515 |
| 5,392,784 A | 2/1995 | Gudaitis | |
| D357,069 S | 4/1995 | Plahn et al. | |
| 5,402,780 A | 4/1995 | Faasse, Jr. | |
| 5,402,884 A | 4/1995 | Gilman et al. | |
| 5,458,141 A | 10/1995 | Neil | |
| 5,473,537 A | 12/1995 | Glazer et al. | |
| 5,511,553 A | 4/1996 | Segalowitz | |
| 5,579,919 A | 12/1996 | Gilman et al. | |
| 5,582,181 A | 12/1996 | Ruess | |
| D377,983 S | 2/1997 | Sabri et al. | |
| 5,601,089 A | 2/1997 | Bledsoe et al. | |
| 5,623,935 A | 4/1997 | Faisandier | |
| 5,682,901 A * | 11/1997 | Kamen | A61B 5/0468 600/519 |
| 5,697,955 A | 12/1997 | Stolte | |
| 5,749,902 A | 5/1998 | Olsen et al. | |
| 5,817,151 A | 10/1998 | Olsen et al. | |
| 5,819,741 A | 10/1998 | Karlsson et al. | |
| 5,850,920 A | 12/1998 | Gilman et al. | |
| D407,159 S | 3/1999 | Roberg | |
| 5,906,583 A | 5/1999 | Rogel | |
| 5,951,598 A | 9/1999 | Bishay et al. | |
| 5,957,857 A | 9/1999 | Hartley | |
| 5,984,102 A | 11/1999 | Tay | |
| 6,032,064 A | 2/2000 | Devlin et al. | |
| 6,038,469 A | 3/2000 | Karlsson et al. | |
| 6,101,413 A | 8/2000 | Olson et al. | |
| 6,115,638 A | 9/2000 | Groenke | |
| 6,117,077 A | 9/2000 | Del Mar et al. | |
| 6,134,479 A | 10/2000 | Brewer et al. | |
| 6,148,233 A | 11/2000 | Owen et al. | |
| 6,149,602 A | 11/2000 | Arcelus | |
| 6,188,407 B1 * | 2/2001 | Smith | A61B 5/044 345/902 |
| D443,063 S | 5/2001 | Pisani et al. | |
| D445,507 S | 7/2001 | Pisani et al. | |
| 6,269,267 B1 | 7/2001 | Bardy et al. | |
| 6,272,385 B1 | 8/2001 | Bishay et al. | |
| 6,298,255 B1 | 10/2001 | Cordero et al. | |
| 6,301,502 B1 | 10/2001 | Owen et al. | |
| 6,304,773 B1 | 10/2001 | Taylor et al. | |
| 6,304,780 B1 | 10/2001 | Owen et al. | |
| 6,304,783 B1 | 10/2001 | Lyster et al. | |
| 6,374,138 B1 | 4/2002 | Owen et al. | |
| 6,418,342 B1 | 7/2002 | Owen et al. | |
| 6,424,860 B1 | 7/2002 | Karlsson et al. | |
| 6,427,083 B1 | 7/2002 | Owen et al. | |
| 6,456,872 B1 | 9/2002 | Faisandier | |
| 6,546,285 B1 | 4/2003 | Owen et al. | |
| 6,605,046 B1 | 8/2003 | Del Mar | |
| 6,607,485 B2 | 8/2003 | Bardy | |
| 6,611,705 B2 | 8/2003 | Hopman et al. | |
| 6,671,545 B2 | 12/2003 | Fincke | |
| 6,671,547 B2 | 12/2003 | Lyster et al. | |
| 6,694,186 B2 | 2/2004 | Bardy | |
| 6,704,595 B2 | 3/2004 | Bardy | |
| 6,705,991 B2 | 3/2004 | Bardy | |
| 6,719,701 B2 * | 4/2004 | Lade | A61N 1/3622 600/481 |
| 6,754,523 B2 | 6/2004 | Toole | |
| 6,782,293 B2 | 8/2004 | Dupelle et al. | |
| 6,856,832 B1 | 2/2005 | Matsumura | |
| 6,860,897 B2 | 3/2005 | Bardy | |
| 6,866,629 B2 | 3/2005 | Bardy | |
| 6,887,201 B2 | 5/2005 | Bardy | |
| 6,893,397 B2 | 5/2005 | Bardy | |
| 6,904,312 B2 | 6/2005 | Bardy | |
| 6,908,431 B2 | 6/2005 | Bardy | |
| 6,913,577 B2 | 7/2005 | Bardy | |
| 6,944,498 B2 | 9/2005 | Owen et al. | |
| 6,960,167 B2 | 11/2005 | Bardy | |
| 6,978,169 B1 | 12/2005 | Guerra | |
| 6,993,377 B2 | 1/2006 | Flick et al. | |
| 7,020,508 B2 | 3/2006 | Stivoric et al. | |
| 7,027,864 B2 | 4/2006 | Snyder et al. | |
| 7,065,401 B2 | 6/2006 | Worden | |
| 7,085,601 B1 | 8/2006 | Bardy et al. | |
| 7,104,955 B2 | 9/2006 | Bardy | |
| 7,134,996 B2 | 11/2006 | Bardy | |
| 7,147,600 B2 | 12/2006 | Bardy | |
| 7,215,991 B2 | 5/2007 | Besson et al. | |
| 7,248,916 B2 | 7/2007 | Bardy | |
| 7,257,438 B2 | 8/2007 | Kinast | |
| 7,277,752 B2 | 10/2007 | Matos | |
| D558,882 S | 1/2008 | Brady | |
| 7,328,061 B2 | 2/2008 | Rowlandson et al. | |
| 7,412,395 B2 | 8/2008 | Rowlandson et al. | |
| 7,429,938 B1 | 9/2008 | Corndorf | |
| D606,656 S | 12/2009 | Kobayashi et al. | |
| 7,706,870 B2 * | 4/2010 | Shieh | A61B 5/4064 600/521 |
| 7,756,721 B1 | 7/2010 | Falchuk et al. | |
| 7,787,943 B2 | 8/2010 | McDonough | |
| 7,874,993 B2 | 1/2011 | Bardy | |
| 7,881,785 B2 | 2/2011 | Nassif et al. | |
| D639,437 S | 6/2011 | Bishay et al. | |
| 7,959,574 B2 | 6/2011 | Bardy | |
| 8,116,841 B2 | 2/2012 | Bly et al. | |
| 8,172,761 B1 | 5/2012 | Rulkov et al. | |
| 8,180,425 B2 | 5/2012 | Selvitelli et al. | |
| 8,200,320 B2 | 6/2012 | Kovacs | |
| 8,231,539 B2 | 7/2012 | Bardy | |
| 8,231,540 B2 | 7/2012 | Bardy | |
| 8,239,012 B2 | 8/2012 | Felix et al. | |
| 8,249,686 B2 | 8/2012 | Libbus et al. | |
| 8,260,414 B2 | 9/2012 | Nassif et al. | |
| 8,266,008 B1 | 9/2012 | Siegal et al. | |
| 8,277,378 B2 | 10/2012 | Bardy | |
| 8,285,356 B2 | 10/2012 | Bly et al. | |
| 8,285,370 B2 | 10/2012 | Felix et al. | |
| 8,308,650 B2 | 11/2012 | Bardy | |
| 8,366,629 B2 | 2/2013 | Bardy | |
| 8,374,688 B2 | 2/2013 | Libbus et al. | |
| 8,412,317 B2 | 4/2013 | Mazar | |
| 8,460,189 B2 | 6/2013 | Libbus et al. | |
| 8,473,047 B2 | 6/2013 | Chakravarthy et al. | |
| 8,478,418 B2 | 7/2013 | Fahey | |
| 8,554,311 B2 | 10/2013 | Warner et al. | |
| 8,591,430 B2 | 11/2013 | Amurthur et al. | |
| 8,594,763 B1 | 11/2013 | Bibian et al. | |
| 8,613,708 B2 | 12/2013 | Bishay et al. | |

(56) References Cited

U.S. PATENT DOCUMENTS

| | | | |
|---|---|---|---|
| 8,613,709 B2 | 12/2013 | Bishay et al. | |
| 8,620,418 B1* | 12/2013 | Kuppuraj | A61B 5/0404 600/515 |
| 8,626,277 B2 | 1/2014 | Felix et al. | |
| 8,668,653 B2 | 3/2014 | Nagata et al. | |
| 8,684,925 B2 | 4/2014 | Manicka et al. | |
| 8,688,190 B2 | 4/2014 | Libbus et al. | |
| 8,718,752 B2 | 5/2014 | Libbus et al. | |
| 8,744,561 B2 | 6/2014 | Fahey | |
| 8,774,932 B2 | 7/2014 | Fahey | |
| 8,790,257 B2 | 7/2014 | Libbus et al. | |
| 8,790,259 B2 | 7/2014 | Katra et al. | |
| 8,795,174 B2 | 8/2014 | Manicka et al. | |
| 8,798,734 B2 | 8/2014 | Kuppuraj et al. | |
| 8,818,478 B2 | 8/2014 | Scheffler et al. | |
| 8,818,481 B2 | 8/2014 | Bly et al. | |
| 8,823,490 B2 | 9/2014 | Libbus et al. | |
| 9,277,864 B2 | 3/2016 | Yang et al. | |
| 2002/0013538 A1 | 1/2002 | Teller | |
| 2002/0013717 A1 | 1/2002 | Ando et al. | |
| 2002/0103422 A1* | 8/2002 | Harder | A61B 5/044 600/300 |
| 2002/0120310 A1 | 8/2002 | Linden et al. | |
| 2002/0184055 A1 | 12/2002 | Naghavi et al. | |
| 2002/0193668 A1 | 12/2002 | Munneke | |
| 2003/0004547 A1 | 1/2003 | Owen et al. | |
| 2003/0073916 A1 | 4/2003 | Yonce | |
| 2003/0083559 A1 | 5/2003 | Thompson | |
| 2003/0097078 A1* | 5/2003 | Maeda | A61B 5/044 600/509 |
| 2003/0139785 A1 | 7/2003 | Riff et al. | |
| 2003/0176802 A1* | 9/2003 | Galen | A61B 5/044 600/523 |
| 2003/0211797 A1 | 11/2003 | Hill et al. | |
| 2004/0008123 A1 | 1/2004 | Carrender et al. | |
| 2004/0019288 A1 | 1/2004 | Kinast | |
| 2004/0034284 A1 | 2/2004 | Aversano et al. | |
| 2004/0049132 A1 | 3/2004 | Barron et al. | |
| 2004/0073127 A1 | 4/2004 | Istvan et al. | |
| 2004/0087836 A1 | 5/2004 | Green et al. | |
| 2004/0093192 A1* | 5/2004 | Hasson | A61B 5/044 703/1 |
| 2004/0148194 A1 | 7/2004 | Wellons et al. | |
| 2004/0236202 A1 | 11/2004 | Burton | |
| 2004/0243435 A1 | 12/2004 | Williams | |
| 2004/0256453 A1 | 12/2004 | Lammle | |
| 2004/0260188 A1 | 12/2004 | Syed et al. | |
| 2005/0096717 A1 | 5/2005 | Bishay et al. | |
| 2005/0108055 A1 | 5/2005 | Ott et al. | |
| 2005/0154267 A1 | 7/2005 | Bardy | |
| 2005/0182308 A1 | 8/2005 | Bardy | |
| 2005/0182309 A1 | 8/2005 | Bardy | |
| 2005/0215918 A1 | 9/2005 | Frantz et al. | |
| 2005/0228243 A1 | 10/2005 | Bardy | |
| 2005/0245839 A1 | 11/2005 | Stivoric et al. | |
| 2006/0025696 A1 | 2/2006 | Kurzweil et al. | |
| 2006/0025824 A1 | 2/2006 | Freeman et al. | |
| 2006/0041201 A1 | 2/2006 | Behbehani et al. | |
| 2006/0122469 A1 | 6/2006 | Martel | |
| 2006/0224072 A1 | 10/2006 | Shennib | |
| 2006/0235320 A1 | 10/2006 | Tan et al. | |
| 2006/0253006 A1 | 11/2006 | Bardy | |
| 2006/0264730 A1 | 11/2006 | Stivoric et al. | |
| 2007/0003115 A1 | 1/2007 | Patton et al. | |
| 2007/0050209 A1 | 3/2007 | Yered | |
| 2007/0078324 A1 | 4/2007 | Wijisiriwardana | |
| 2007/0093719 A1 | 4/2007 | Nichols, Jr. et al. | |
| 2007/0100248 A1* | 5/2007 | Van Dam | A61B 5/02405 600/515 |
| 2007/0100667 A1 | 5/2007 | Bardy | |
| 2007/0123801 A1 | 5/2007 | Goldberger et al. | |
| 2007/0136091 A1 | 6/2007 | McTaggart | |
| 2007/0179357 A1 | 8/2007 | Bardy | |
| 2007/0185390 A1 | 8/2007 | Perkins et al. | |
| 2007/0203415 A1 | 8/2007 | Bardy | |
| 2007/0203423 A1 | 8/2007 | Bardy | |
| 2007/0208233 A1 | 9/2007 | Kovacs | |
| 2007/0208266 A1* | 9/2007 | Hadley | A61B 5/02405 600/519 |
| 2007/0225611 A1 | 9/2007 | Kumar et al. | |
| 2007/0244405 A1 | 10/2007 | Xue et al. | |
| 2007/0249946 A1 | 10/2007 | Kumar et al. | |
| 2007/0255153 A1 | 11/2007 | Kumar et al. | |
| 2007/0265510 A1 | 11/2007 | Bardy | |
| 2007/0276270 A1 | 11/2007 | Tran | |
| 2007/0276275 A1* | 11/2007 | Proctor | A61B 5/02405 600/513 |
| 2007/0293738 A1 | 12/2007 | Bardy | |
| 2007/0293739 A1 | 12/2007 | Bardy | |
| 2007/0293740 A1 | 12/2007 | Bardy | |
| 2007/0293741 A1 | 12/2007 | Bardy | |
| 2007/0293772 A1 | 12/2007 | Bardy | |
| 2007/0299325 A1 | 12/2007 | Farrell et al. | |
| 2008/0051668 A1 | 2/2008 | Bardy | |
| 2008/0058661 A1 | 3/2008 | Bardy | |
| 2008/0091097 A1 | 4/2008 | Linti et al. | |
| 2008/0139953 A1 | 6/2008 | Baker et al. | |
| 2008/0194927 A1 | 8/2008 | KenKnight et al. | |
| 2008/0208009 A1 | 8/2008 | Shklarski | |
| 2008/0208014 A1 | 8/2008 | KenKnight et al. | |
| 2008/0284599 A1 | 11/2008 | Zdeblick et al. | |
| 2008/0288026 A1 | 11/2008 | Cross et al. | |
| 2008/0306359 A1 | 12/2008 | Zdeblick et al. | |
| 2009/0054952 A1 | 2/2009 | Glukhovsky et al. | |
| 2009/0069867 A1 | 3/2009 | KenKnight et al. | |
| 2009/0073991 A1 | 3/2009 | Landrum et al. | |
| 2009/0076336 A1 | 3/2009 | Mazar et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076346 A1 | 3/2009 | James et al. | |
| 2009/0076349 A1 | 3/2009 | Libbus et al. | |
| 2009/0076397 A1 | 3/2009 | Libbus et al. | |
| 2009/0076401 A1 | 3/2009 | Mazar et al. | |
| 2009/0076559 A1 | 3/2009 | Libbus et al. | |
| 2009/0112116 A1 | 4/2009 | Lee et al. | |
| 2009/0131759 A1 | 5/2009 | Sims et al. | |
| 2009/0216132 A1 | 8/2009 | Orbach | |
| 2009/0270708 A1 | 10/2009 | Shen et al. | |
| 2009/0270747 A1 | 10/2009 | Van Dam et al. | |
| 2009/0292194 A1 | 11/2009 | Libbus et al. | |
| 2010/0022897 A1 | 1/2010 | Parker et al. | |
| 2010/0056881 A1 | 3/2010 | Libbus et al. | |
| 2010/0081913 A1 | 4/2010 | Cross et al. | |
| 2010/0185063 A1 | 7/2010 | Bardy | |
| 2010/0185076 A1 | 7/2010 | Jeong et al. | |
| 2010/0191154 A1 | 7/2010 | Berger et al. | |
| 2010/0191310 A1 | 7/2010 | Bly | |
| 2010/0234715 A1 | 9/2010 | Shin et al. | |
| 2010/0234716 A1 | 9/2010 | Engel | |
| 2010/0324384 A1 | 12/2010 | Moon et al. | |
| 2011/0054286 A1 | 3/2011 | Crosby et al. | |
| 2011/0066041 A1* | 3/2011 | Pandia | A61B 5/113 600/484 |
| 2011/0077497 A1 | 3/2011 | Oster et al. | |
| 2011/0144470 A1 | 6/2011 | Mazar et al. | |
| 2011/0160548 A1 | 6/2011 | Forster | |
| 2011/0224564 A1 | 9/2011 | Moon et al. | |
| 2011/0237924 A1 | 9/2011 | McGusty et al. | |
| 2011/0245711 A1 | 10/2011 | Katra et al. | |
| 2012/0003933 A1 | 1/2012 | Baker et al. | |
| 2012/0029306 A1 | 2/2012 | Paquet et al. | |
| 2012/0029316 A1 | 2/2012 | Raptis et al. | |
| 2012/0035432 A1 | 2/2012 | Katra et al. | |
| 2012/0088998 A1 | 4/2012 | Bardy et al. | |
| 2012/0088999 A1 | 4/2012 | Bishay et al. | |
| 2012/0089000 A1 | 4/2012 | Bishay et al. | |
| 2012/0089001 A1 | 4/2012 | Bishay et al. | |
| 2012/0089037 A1 | 4/2012 | Bishay et al. | |
| 2012/0089412 A1 | 4/2012 | Bardy et al. | |
| 2012/0089417 A1 | 4/2012 | Bardy et al. | |
| 2012/0095352 A1 | 4/2012 | Tran | |
| 2012/0101358 A1 | 4/2012 | Boettcher et al. | |
| 2012/0101396 A1 | 4/2012 | Solosko et al. | |

(56) References Cited

U.S. PATENT DOCUMENTS

| | | | |
|---|---|---|---|
| 2012/0302906 A1 | 11/2012 | Felix et al. | |
| 2013/0079611 A1 | 3/2013 | Besko | |
| 2013/0085403 A1* | 4/2013 | Gunderson | A61B 5/044 |
| | | | 600/510 |
| 2013/0096395 A1 | 4/2013 | Katra et al. | |
| 2013/0116533 A1 | 5/2013 | Lian et al. | |
| 2013/0123651 A1 | 5/2013 | Bardy | |
| 2013/0158361 A1 | 6/2013 | Bardy | |
| 2013/0243105 A1 | 9/2013 | Lei et al. | |
| 2013/0274584 A1 | 10/2013 | Finlay et al. | |
| 2013/0275158 A1 | 10/2013 | Fahey | |
| 2013/0331665 A1 | 12/2013 | Libbus et al. | |
| 2013/0338448 A1 | 12/2013 | Libbus et al. | |
| 2014/0012154 A1 | 1/2014 | Mazar et al. | |
| 2014/0140359 A1 | 5/2014 | Kalevo et al. | |
| 2014/0189928 A1 | 7/2014 | Oleson et al. | |
| 2014/0206977 A1 | 7/2014 | Bahney et al. | |
| 2015/0048836 A1 | 2/2015 | Guthrie et al. | |
| 2015/0165211 A1 | 6/2015 | Naqvi et al. | |
| 2015/0257670 A1 | 9/2015 | Ortega et al. | |
| 2015/0359489 A1 | 12/2015 | Baudenbacher et al. | |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| WO | 0078213 | 12/2000 |
| WO | 03032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2009036306 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2011047207 | 4/2011 |
| WO | 2012140559 | 10/2012 |
| WO | 2012146957 | 11/2012 |

OTHER PUBLICATIONS 15 of the Hottest Wearable Gadgets, URL <http://thehottestgadgets.com/2008/09/the-15-hottest-wearable-gadgets-001253> (Web page cached on Sep. 27, 2008).

Alivecor's Heart Monitor for iPhone Receives FDA Clearance, URL <http://www.businesswire.com/news/home/20121203005545/en/AliveCor%E2%80%99s-Heart-Monitor-iPhone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al., "Monitoring Body Temperature of Newborn Infants at Neonatal Intensive Care Units Using Wearable Sensors," BodyNets 2010, Corfu Island, Greece. (Sep. 10, 2010).

Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs, May 2008.

Fitbit automatically tracks your fitness and sleep, URL <http://www.fitbit.com/> (Web page cached on Sep. 10, 2008).

Smith, Kevin, "Jawbone Up VS. Fitbit Flex: Which is the Best Fitness Band?" URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

Lauren Gravitz, "When Your Diet Needs a Band-Aid, "Technology Review, MIT. (May 1, 2009).

Lieberman, Jonathan, "How Telemedicine is Aiding Prompt ECG Diagnosis in Primary Care," British Journal of Community Nursing, vol. 13, No. 3, Mar. 1, 2008, pp. 123-126, XP009155082, ISSN: 1462-4753.

McManus et al., "A Novel Application for the Detection of an Irregular Pulse using an iPhone 4S in Patients with Atrial Fibrillation," vol. 10(3), pp. 315-319 (Mar. 2013).

Nike+ Fuel Band, URL <http://www.nike.com/us/en_us/c/nikeplusfuelband> (Web page cached on Jan. 11, 2013).

P. Libby et al.,"Braunwald's Heart Disease—A Textbook of Cardiovascular Medicine," Chs. 11, pp. 125-148 and 12, pp. 149-193 (8th ed. 2008), American Heart Association.

Initial hands-on with Polar Loop activity tracker, URL <http://www.dcrainmakercom/2013/09/polar-loop-firstlook.html> (Sep. 17, 2013).

Sittig et al., "A Computer-Based Outpatient Clinical Referral System," International Journal of Medical Informatics, Shannon, IR, vol. 55, No. 2, Aug. 1, 1999, pp. 149-158, X0004262434, ISSN: 1386-5056(99)00027-1.

Sleepview, URL <http://www.clevemed.com/sleepview/overview.shtml> (Web pages cached on Feb. 23, 2010, Dec. 29, 2012 and Sep. 4, 2013).

Actigraphy/Circadian Rhythm SOMNOwatch, URL <http://www.somnomedics.eu/news-events/publications/somnowatchtm.html> (Web page cached on Jan. 23, 2010).

Zio Event Card, URL <http://www.irhythmtech.com/zio-solution/zio-event/> (Web page cached on Mar. 11, 2013).

Zio Patch System, URL <http://www.irhythmtech.com/zio-solution/zio-system/index.html> (Web page cached on Sep. 8, 2013).

Seifert, Dan, "Samsung dives into fitness wearable with the Gear Fit/The Verge," URL <http://www.theverge.com/2014/2/24/5440310/samsung-dives-into-fitness-wearables-with-the-gear-fit> (Feb. 24, 2014).

Soper, Taylor, "Samsung's new Galaxy S5 flagship phone has fingerprint reader, heart rate monitor," URL <http://www.geekwire.com/2014/samsung-galaxy-s5-fingerprint> (Feb. 24, 2014).

Dolcourt, Jessica, "See the Samsung Galaxy S5's Heart rate monitor in action," URL <http://www.cnet.com/news/see-the-samsung-galaxy-s5s-heart-rate-monitor-in-action> (Feb. 25, 2014).

Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.

Anonymous. Omegawave Launches Consumer App 2.0 in U.S. "Endurance Sportswire—Endurance Sportswire." Jul. 11, 2013. URL:http://endurancesportswire.com/omegawave-launches-consumer-app-2-0-in-u-s/.

Chan et al. "Wireless Patch Sensor for Remote Monitoring of Heart Rate, Respiration, Activity, and Falls." pp. 5115-6118. 2013 35th Annual International Conference of the IEEE Engineering in Medical and Biology Society. Jul. 1, 2013.

Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.

Daoud et al. "Fall Detection Using Shimmer Technology and Multiresolution Analysis." Aug. 2, 2013. URL: https://decibel.ni.com/content/docs/DOC-26652.

Libbus. "Adherent Cardiac Monitor With Wireless Fall Detection for Patients With Unexplained Syncope." Abstracts of the First AMA-IEEE Medical Technology Conference on Individualized Healthcare. May 22, 2010.

Health Research—Hexoskin Biometric Shirt | Hexoskin URL:http://www.hexoskin.com/pages/health-research (Web page cached on Dec. 2, 2014).

Jacob Kastrenakes, "Apple Watch uses four sensors to detect your pulse," Sep. 9, 2014. URL: http://www.theverge.com/2014/9/9/6126991/apple-watch-four-back-sensors-detect-activity.

(56) References Cited

OTHER PUBLICATIONS

Nicole Lee, "Samsung Gear S review: an ambitious and painfully flawed smartwatch," Dec. 1, 2014. URL: http://www.engadget.com/2014/12/01/samsung-gear-s-review/.

Duttweiler et al., "Probability Estimation in Arithmetic and Adaptive-Huffman Entropy Coders," IEEE Transactions on Image Processing. vol. 4, No. 3, Mar. 1, 1995, pp. 237-246.

Gupta et al., "An ECG Compression Technique for Telecardiology Application," India Conference (INDICON), 2011 Annual IEEE, Dec. 16, 2011, pp. 1-4.

Nave et al., "ECG Compression Using Long-Term Prediction," IEEE Transactions on Biomedical Engineering, IEEE Service Center, NY, USA, vol. 40, No. 9, Sep. 1, 1993, pp. 877-885.

Skretting et al., "Improved Huffman Coding Using Recursive Splitting," NORSIG, Jan. 1, 1999.

* cited by examiner

SYSTEM AND METHOD FOR FACILITATING DIAGNOSIS OF CARDIAC RHYTHM DISORDERS WITH THE AID OF A DIGITAL COMPUTER

CROSS-REFERENCE TO RELATED APPLICATION

This non-provisional patent application is a continuation-in-part of U.S. patent application Ser. No. 14/997,416, filed Jan. 15, 2016, now U.S. Pat. No. 9,345,414, which is a continuation-in-part of U.S. patent application Ser. No. 14/614,265, filed Feb. 4, 2015, pending; which is a continuation-in-part of U.S. patent application Ser. No. 14/488,230, filed Sep. 16, 2014, pending; which is a continuation-in-part of U.S. patent application Ser. No. 14/080,725, filed Nov. 14, 2013, pending, and further claims priority under 35 U.S.C. §119(e) to U.S. Provisional Patent application, Ser. No. 62/132,497, filed Mar. 12, 2015, the disclosures of which are incorporated by reference.

FIELD

This application relates in general to electrocardiographic monitoring and, in particular, to a method for facilitating diagnosis of cardiac rhythm disorders with the aid of a digital computer.

BACKGROUND

An electrocardiogram (ECG) allows physicians to diagnose cardiac function by visually tracing the cutaneous electrical signals (action potentials) that are generated by the propagation of the transmembrane ionic currents that trigger the depolarization of cardiac fibers. An ECG trace contains alphabetically-labeled waveform deflections that represent distinct features within the cyclic cardiac activation sequence. The P-wave represents atrial depolarization, which causes atrial contraction. The QRS-complex represents ventricular depolarization. The T-wave represents ventricular repolarization.

The R-wave is often used as an abbreviation for the QRS-complex. An R-R interval spans the period between successive R-waves and, in a normal heart, is 600 milliseconds (ms) to one second long, which respectively correspond to 100 to 60 beats per minute (bpm). The R-wave is the largest waveform generated during normal conduction and represents the cardiac electrical stimuli passing through the ventricular walls. R-R intervals provide information that allows a physician to understand at a glance the context of cardiac rhythms both before and after a suspected rhythm abnormality and can be of confirmational and collaborative value in cardiac arrhythmia diagnosis and treatment.

Conventionally, the potential of R-R interval context has not been fully realized, partly due to the difficulty of presentation in a concise and effective manner to physicians. For instance, routine ECGs are typically displayed at an effective paper speed of 25 millimeters (mm) per second. A lower speed is not recommended because ECG graph resolution degrades at lower speeds and diagnostically-relevant features may be lost. Conversely, a half-hour ECG recording, progressing at 25 mm/s, results in 45 meters of ECG waveforms that, in printed form, is cumbersome and, in electronic display form, will require significant back and forth toggling between pages of waveforms, as well as presenting voluminous data transfer and data storage concerns. As a result, ECGs are less than ideal tools for diagnosing cardiac arrhythmia patterns that only become apparent over an extended time frame, such as 30 minutes or longer.

R-R intervals have also been visualized in Poincaré plots, which graph RR(n) on the x-axis and RR(n+1) on the y-axis. However, a Poincaré plot fails to preserve the correlation between an R-R interval and the R-R interval's time of occurrence and the linearity of time and associated contextual information, before and after a specific cardiac rhythm, are lost. In addition, significant changes in heart rate, particularly spikes in heart rate, such as due to sinus rhythm transitions to atrial flutter or atrial fibrillation, may be masked or distorted in a Poincaré plot if the change occurs over non-successive heartbeats, rather than over two adjacent heartbeats, which undermines reliance on Poincaré plots as dependable cardiac arrhythmia diagnostic tools. Further, Poincare plots cannot provide context and immediate temporal reference to the actual ECG, regardless of paper speed. Events both prior to and after a specific ECG rhythm can provide key clinical information disclosed in the R-R interval plot that may change patient management above and beyond the specific rhythm being diagnosed.

Therefore, a need remains for presenting R-R interval data to physicians to reveal temporally-related patterns as an aid to rhythm abnormality diagnosis.

SUMMARY

R-R interval data is presented to physicians in a format that includes views of relevant near field and far field ECG data, which together provide contextual information that improves diagnostic accuracy. The near field (or short duration) ECG data view provides a "pinpoint" classical view of an ECG at traditional recording speed in a manner that is known to and widely embraced by physicians. The near field ECG data is coupled to a far field (or medium duration) ECG data view that provides an "intermediate" lower resolution, pre- and post-event contextual view.

Both near field and far field ECG data views are temporally keyed to an extended duration R-R interval data view. In one embodiment, the R-R interval data view is scaled non-linearly to maximize the visual differentiation for frequently-occurring heart rate ranges, such that a single glance allows the physician to make a diagnosis. All three views are presented simultaneously, thereby allowing an interpreting physician to diagnose rhythm and the pre- and post-contextual events leading up to a cardiac rhythm of interest.

The durations of the classical "pinpoint" view, the pre- and post-event "intermediate" view, and the R-R interval plot are flexible and adjustable. In one embodiment, a temporal point of reference is identified in the R-R interval plot and the ECG data that is temporally associated with the point of reference is displayed in the near field and far field ECG data views. In a further embodiment, diagnostically relevant cardiac events can be identified as the temporal point of reference. For clarity, the temporal point of reference will generally be placed in the center of the R-R interval data to allow pre- and post-event heart rhythm and ECG waveform data to present in the correct context. Thus, the pinpoint "snapshot" and intermediate views of ECG data with the extended term R-R interval data allow a physician to comparatively view heart rate context and patterns of behavior prior to and after a clinically meaningful arrhythmia, patient concern or other indicia, thereby enhancing diagnostic specificity of cardiac rhythm disorders and providing physiological context to improve diagnostic ability.

One embodiment provides a system and method for facilitating diagnosis of cardiac rhythm disorders with the aid of a digital computer. Cutaneous action potentials of a patient are monitored and recorded. The cutaneous action potentials are retrieved as electrocardiogram (ECG) data for a set time period and a plurality of R-wave peaks in the ECG data are identified. A difference between recording times of successive pairs of the R-wave peaks is calculated and a heart rate associated with each time difference is determined. An extended duration R-R interval plot over the set time period is formed and includes each of the recording time differences and the associated heart rates. The extended duration R-R interval plot is displayed and a temporal point of reference in the extended duration R-R interval plot is identified. At least part of the ECG data preceding and following the temporal point of reference is displayed as context in at least one accompanying ECG plot.

The foregoing aspects enhance the presentation of diagnostically relevant R-R interval data, reduce time and effort needed to gather relevant information by a clinician and provide the clinician with a concise and effective diagnostic tool, which is critical to accurate arrhythmia and cardiac rhythm disorder diagnoses.

Custom software packages have been used to identify diagnostically relevant cardiac events from the electrocardiography data, but usually require a cardiologist's diagnosis and verification. In contrast, when presented with a machine-identified event, the foregoing approach aids the cardiologist's diagnostic job by facilitating presentation of ECG-based background information prior to and after the identified event.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, including time and clustering of events, all without departing from their spirit and the scope. Accordingly, the drawings and detailed description are to be regarded as illustrative in nature and not as restrictive.

DETAILED DESCRIPTION

A normal healthy cardiac cycle repeats through an expected sequence of events that can be visually traced through an ECG. Each cycle starts with cardiac depolarization originating high in the right atrium in the sinoatrial (SA) node before spreading leftward towards the left atrium and inferiorly towards the atrioventricular (AV) node. After a delay in the AV node, the depolarization impulse transits the Bundle of His and moves into the right and left bundle branches and Purkinje fibers to activate the right and left ventricles.

Figure 1:
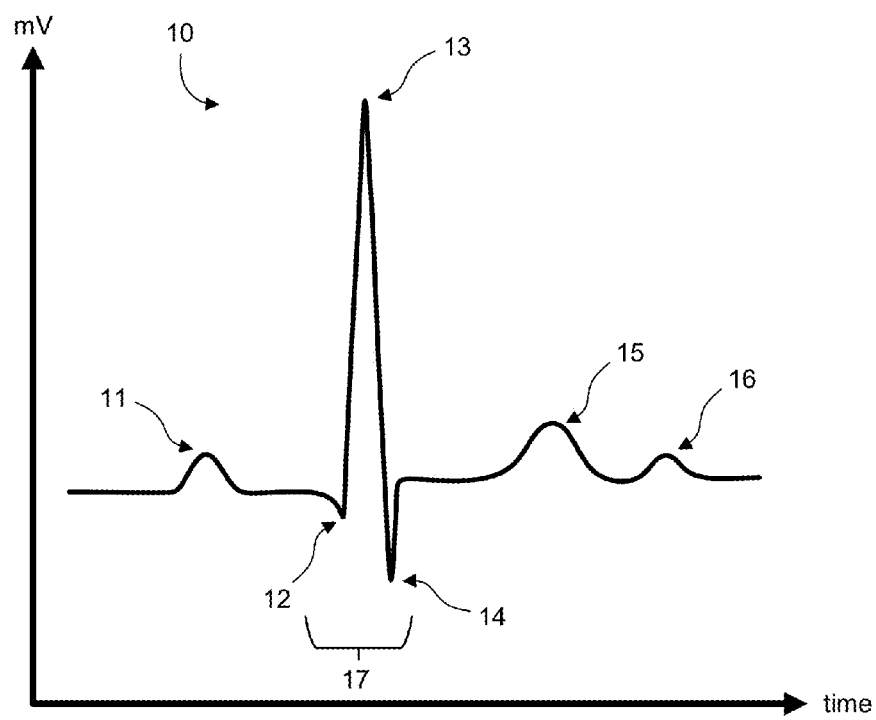
FIG. 1 is a graph showing, by way of example, a single ECG waveform.

When a rhythm disorder is suspected, diagnostically-relevant arrhythmic events in the cardiac cycle can often be identified and evaluated with the assistance of an ECG and R-R interval tachography, such as Poincaré plots. Routine ECG evaluation is primarily focused identifying changes to expected ECG waveform shapes. FIG. 1 is a graph showing, by way of example, a single ECG waveform 10. The x-axis represents approximate time in units of tenths of a second and the y-axis represents approximate cutaneous electrical signal strength in units of millivolts. By long-standing convention, ECGs are typically printed or displayed at an effective paper speed of 25 millimeters (mm) per second. Although in practice an ECG may be provided to a physician in traditional paper-printed form, in "virtual" electronic display form, or both, the term "effective paper speed" is nevertheless still widely applied as a metric to normalize the recorded ECG signal to a standardized grid of 1 mm squares (omitted for the sake of clarity in FIG. 1), whereby each 1 mm horizontal box in the grid corresponds to 0.04 s (40 ms) of recorded time. Other effective paper speeds, grid sizes and units of display are possible.

A full ECG consists of a stream of alphabetically-labeled waveforms 10 that collectively cover cardiac performance over a period of observation. For a healthy patient, within each ECG waveform 10, the P-wave 11 will normally have a smooth, normally upward, positive waveform that indicates atrial depolarization. The QRS complex 17 will usually follow, often with a downward deflection of a Q-wave 12, followed by a larger upward deflection of an R-wave 13, and be terminated with a downward waveform of the S-wave 14, which are collectively representative of ventricular depolarization. The T-wave 15 will normally be a modest upward waveform, representative of ventricular repolarization, while the U-wave 16, which is often not directly observable, will indicate the recovery period of the Purkinje conduction fibers.

Rhythm disorders often manifest through R-R interval variability and the patterns formed by R-R intervals over an extended time period are important tools in the diagnosis of cardiac rhythm abnormalities. For example, atrial fibrillation (AF) is the chaotic firing of the atria that leads to an erratic activation of the ventricles. AF is initially diagnosed by an absence of organized P-waves 11 and confirmed by erratic ventricular rates that manifest in an ECG R-R interval plot as a cloud-like pattern of irregular R-R intervals due to an abnormal conduction of impulses to the ventricles. There is a Gaussian-like distribution to these R-R intervals during AF. Similarly, atrial flutter (AFL) is an abnormal heart rhythm in which cardiac impulses travel along pathways within the right atrium in an organized circular motion, causing the atria to beat faster than and out of sync with the ventricles. During AFL, the heart beats quickly, yet with a regular pattern. Although AFL presents in an electrogram (e-gram) as a "sawtooth" pattern, AFL can be confirmed in an ECG by characteristic R-R interval patterns that usually manifest as 2:1 atrioventricular (AV) conduction or 4:1 atrioventricular conduction. On occasion, the conduction through the AV node is variable and not fixed.

Figure 2:
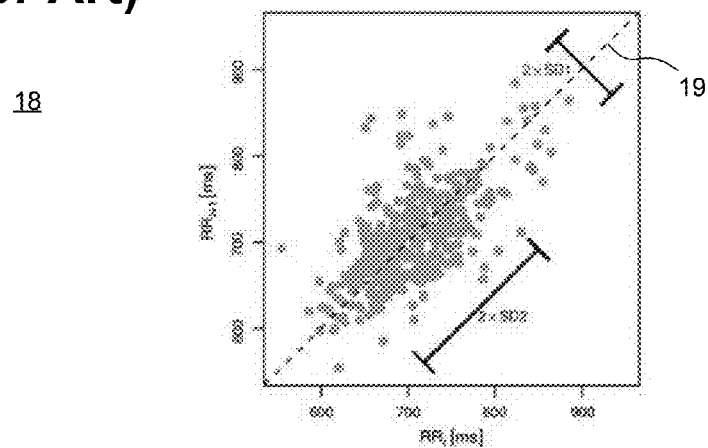
FIG. 2 is a graph showing, by way of example, a prior art Poincaré R-R interval plot.

Conventionally, R-R intervals have been visualized using Poincaré plots. FIG. 2 is a graph showing, by way of example, a prior art Poincaré R-R interval plot 18. The x-axis represents the duration of R-R interval n in units of milliseconds (ms). The y-axis represents the duration of R-R interval n+1 also in units of ms. Ordinarily, the x- and y-axes use the same units, so as to form a trend line 19 along the 45-degree angle. When an R-R interval is equal to the successive R-R interval, as often occurs when heart rhythm is regular, the dot representing the two intervals falls onto the 45-degree trend line 19. Conversely, when an R-R interval has changed since the preceding R-R interval, the dot representing the two intervals falls off the 45-degree trend line 19 and, as the difference between successive R-R intervals increases, the dots fall further away from the trend line 19.

The number of dots deviating from the trend line 19 in a Poincaré plot can indicate the frequency of occurrence of irregular heartbeats when compared to the number of dots on the trend line 19. The distance of the dots to the trend line 19 can approximate the extent of heart rate change from one heartbeat to the next. However, as heart rate change is limited to only successively-occurring heartbeats, the linearity of time and associated contextual information over an extended time frame are lost. In addition, significant changes in heart rate, particularly spikes in heart rate, such as due to sinus rhythm transitions to atrial flutter, may be masked, distorted or even omitted in a Poincaré plot if the change occurs over non-successive heartbeats. In summary, a Poincaré plot is more useful as a mathematical tool than a physiological one, and therefore a Poincaré plot cannot truly represent what the heart is doing serially over time with respect to changes in the heart's normal and abnormal physiology.

Figure 3:
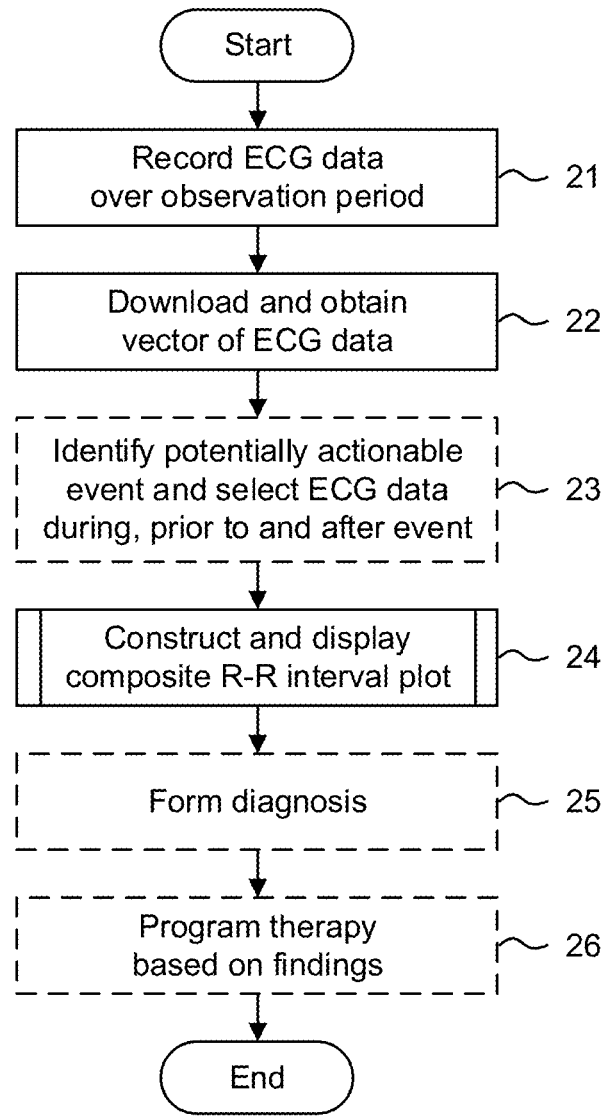
FIG. 3 is a flow diagram showing a method for facilitating diagnosis of cardiac rhythm disorders with the aid of a digital computer in accordance with one embodiment.

Despite the limitations of Poincaré plots and related forms of R-R interval tachography, R-R interval data when presented in a format duplicating temporal physiological events remains a key tool that physicians can rely upon to identify temporally-related cardiac dysrhythmic patterns. Interpretation of R-R interval data can be assisted by including multiple temporal points of reference and a plot of R-R interval data that comparatively depicts heart rate variability in concert with R-R interval data. FIG. 3 is a flow diagram showing a method 20 for facilitating diagnosis of cardiac rhythm disorders with the aid of a digital computer in accordance with one embodiment. The method 20 can be implemented in software and execution of the software can be performed on a computer, such as further described infra with reference to FIG. 14, as a series of process or method modules or steps.

As a precursor step, the cutaneous action potentials of a patient are monitored and recorded as ECG data over a set time period (step 21), which can be over a short term or extended time frame. ECG recordation, as well as physiological monitoring, can be provided through various kinds of ECG-capable monitoring ensembles, including a standardized 12-lead ECG setup, such as used for clinical ECG monitoring, a portable Holter-type ECG recorder for traditional ambulatory ECG monitoring, or a wearable ambulatory ECG monitor, such as a flexible extended wear electrode patch and a removable reusable (or single use) monitor recorder, such as described in commonly-assigned U.S. patent application, entitled "Method for Providing Dynamic Gain over Electrocardiographic Data with the aid of a Digital Computer," Ser. No. 14/997,416, filed Jan. 15, 2016, now U.S. Pat. No. 9,345,414, the disclosure of which is incorporated by reference, the latter of which includes an electrode patch and monitor recorder that are synergistically optimized to capture electrical signals from the propagation of low amplitude, relatively low frequency content cardiac action potentials, particularly the P-waves, generated during atrial activation. Still other forms of ECG monitoring assembles are possible.

Figure 14:
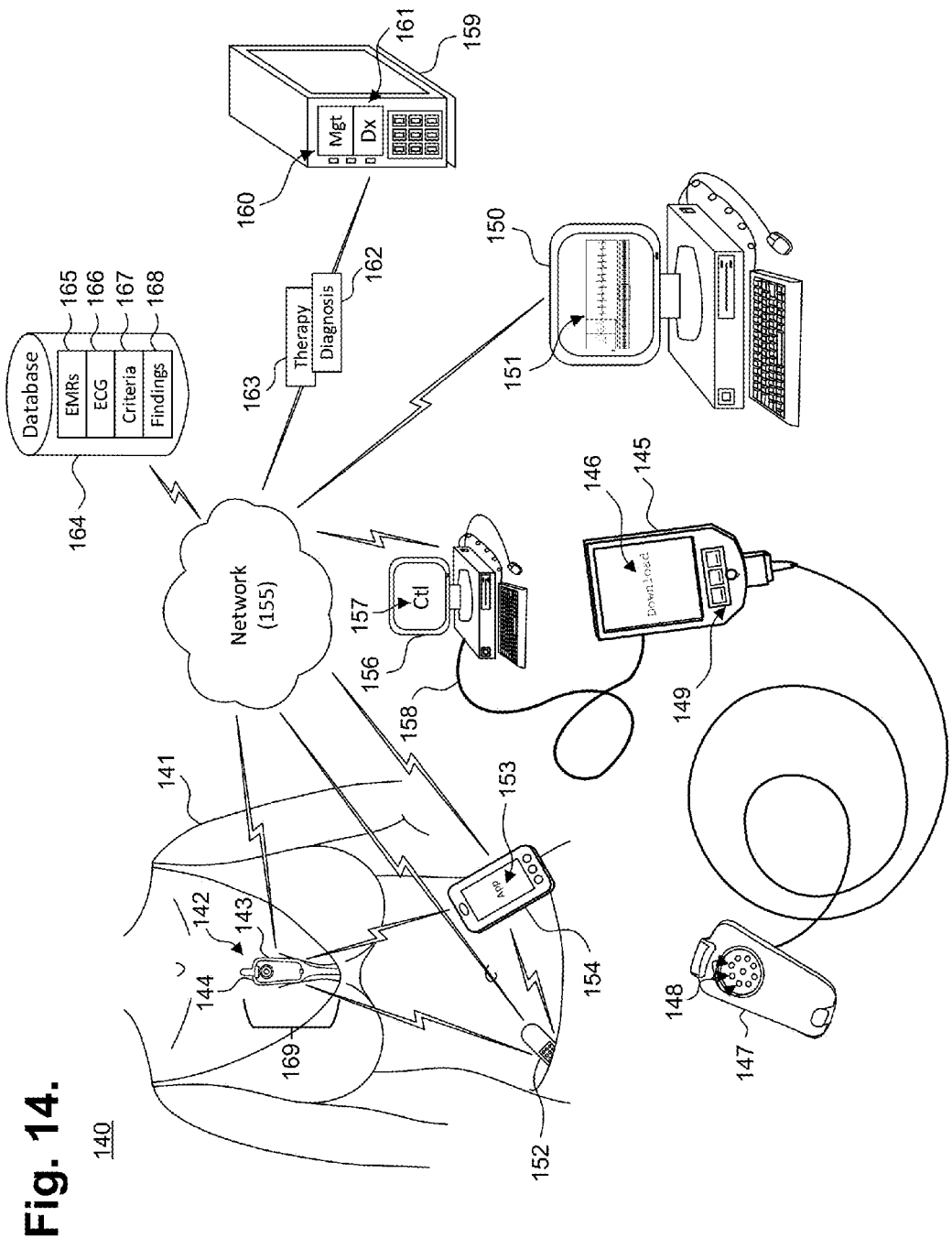
FIG. 14 is a block diagram showing a system for facilitating diagnosis of cardiac rhythm disorders with the aid of a digital computer in accordance with one embodiment.

Upon completion of the monitoring period, the ECG and any physiological data are downloaded or retrieved into a digital computer, as further described infra with reference to FIG. 14, with, for instance, the assistance of a download station or similar device, or via wireless connection, if so equipped, and a vector of the downloaded or retrieved ECG data is obtained (step 22). In one embodiment, the vector of ECG data represents a 40-minute (or other duration) time span that is used in constructing the plot of R-R interval data, although other pre-event and post-event time spans are possible. Optionally, a potentially-actionable cardiac event within the vector of ECG data can be identified and the ECG data during, prior to and after the event is selected (step 23). The event could be identified with the assistance of a software package, such as Holter LX Analysis Software, licensed by NorthEast Monitoring, Inc., Maynard, Mass.; IntelliSpace Cardiovascular Image and Information management system, licensed Koninklijke Philips N.V., Amsterdam, Netherlands; MoMe System, licensed by InfoBionic, Lowell, Mass.; Pyramis ECG Management, licensed by Mortara Instrument Inc., Milwaukee, Wis.; ICS Clinical Suite, licensed by Spacelabs Healthcare Inc., Snoqualmie, Wash.; or a customized software package. Alternatively, the potentially-actionable cardiac event could be identified by a physician or technician during review of the ECG data.

Figure 4:
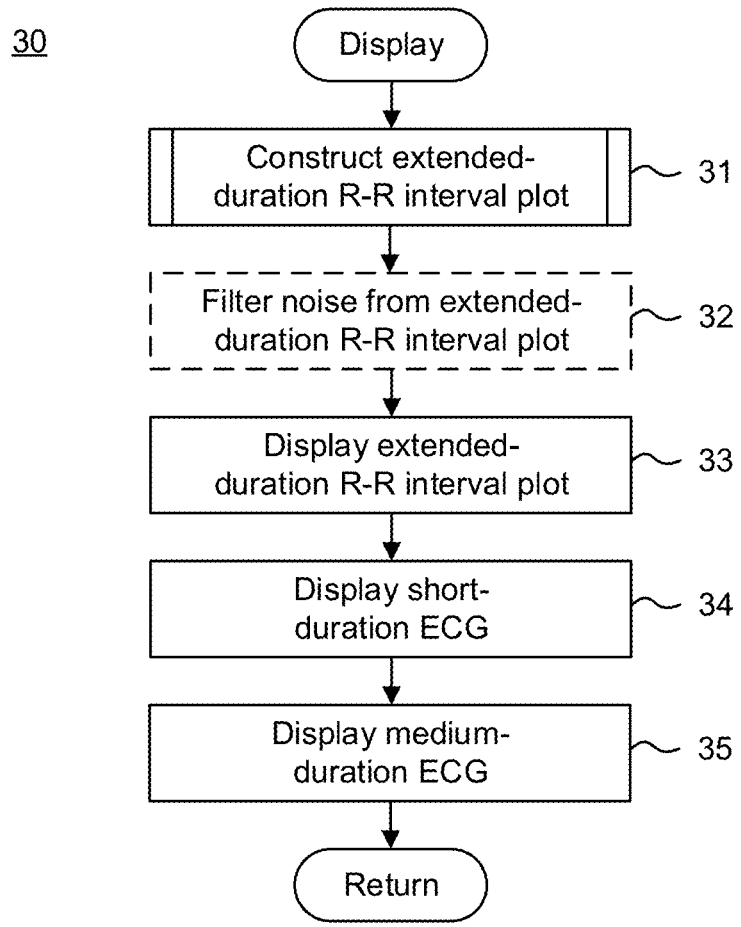
FIG. 4 is a flow diagram showing a routine for constructing and displaying a diagnostic composite plot for use in the method of FIG. 3.

To improve diagnosis of heart rate variability, a diagnostic composite plot is constructed that includes one or more temporal points of reference into the ECG data, which provide important diagnostic context, and a plot of R-R interval data is constructed based on the vector of ECG data (step 24), as further described infra with reference to FIG. 4. Briefly, both near field and far field contextual views of the ECG data are constructed and displayed. Both views are temporally keyed to an extended duration R-R interval data view that, in one embodiment, is scaled non-linearly to maximize the visual differentiation for frequently-occurring heart rate ranges, such that a single glance allows the physician to make a diagnosis. All three views are presented simultaneously, thereby allowing the interpreting physician to diagnose rhythm and the pre- and post-contextual events leading up to a cardiac rhythm of interest.

In a further embodiment, findings made through interpretation of heart rate variability patterns in the diagnostic composite plot can be analyzed to form a diagnosis of a cardiac rhythm disorder (step 25), such as the cardiac rhythm disorders listed, by way of example, in Table 1. For instance, the heart rate variability patterns in the diagnostic composite plot could be provided to a system that programmatically detects AF by virtue of looking for the classic Gaussian-type distribution on the "cloud" of heart rate variability formed in the plot of R-R interval data, which can be corroborated by the accompanying contextual ECG data. Finally, therapy to address diagnosed disorder findings can optionally be programmed into a cardiac rhythm therapy delivery device (step 26), such as an implantable medical device (IMD) (not shown), including a pacemaker, implantable cardioverter defibrillator (ICD), or similar devices.

TABLE 1

Cardiac Rhythm Disorders

Normal sinus rhythm
Sinus Bradycardia
Sinus Tachycardia
Premature atrial and ventricular beats
Ectopic atrial tachycardia
Atrial fibrillation
Atrial flutter
Atrial or ventricular bigeminy, trigeminy or quadrigeminy
Sinus Bradycardia
Fusion beats
Interpolated ventricular premature beats
Intraventricular conduction delay
Junctional rhythm
AV Nodal re-entrant tachycardia
AV re-entrant tachycardia
Wolff-Parkinson-White Syndrome and Pre-excitation
Ventricular tachycardia
Accelerated idioventricular rhythm
Cardiac Rhythm Disorders
AV Wenckebach block
AV Type II block
Sinoatrial block A diagnostic composite plot is constructed and displayed to help physicians identify and diagnose temporally-related cardiac dysrhythmic patterns. The diagnostic composite plot includes ECG traces from two or more temporal points of reference and a plot of R-R interval data, although other configurations of ECG data plots when combined with the R-R interval plot will also provide critical information. FIG. 4 is a flow diagram showing a routine 30 for constructing and displaying a diagnostic composite plot for use in the method 20 of FIG. 3. Specific examples of diagnostic composite plots are discussed in detail infra with reference to FIGS. 7-13.

In the diagnostic composite plot, R-R interval data is presented to physicians in a format that includes views of relevant near field and far field ECG data, which together provide contextual information that improves diagnostic accuracy. In a further embodiment, other views of ECG data can be provided in addition to or in lieu of the near field and far field ECG data views. The near field (or short duration) ECG data provides a "pinpoint" classical view of an ECG at traditional recording speed in a manner that is known to and widely embraced by physicians. The near field ECG data is coupled to a far field (or medium duration) ECG data view that provides an "intermediate" lower resolution, pre- and post-event contextual view. Thus, the extended-duration R-R interval plot is first constructed (step 31), as further described infra with reference to FIG. 5. Optionally, noise can be filtered from the R-R interval plot (step 32), which is then displayed (step 33). Noise filtering can include low-pass or high-pass filtering or other forms of signal processing, including automatic gain control, such as described in commonly-assigned U.S. patent application Ser. No. 14/997,416, cited supra.

Rhythm disorders have different weightings depending upon the context with which they occur. In the diagnostic composite plot, the R-R interval data view and the multiple views of the ECG data provide that necessary context. Effectively, the short and medium duration ECG data that accompanies the extended-duration R-R interval plot represents the ECG data "zoomed" in around a temporal point of reference identified in the center (or other location) of the R-R interval plot, thereby providing a visual context to the physician that allows temporal assessment of cardiac rhythm changes in various complementary views of the heart's behavior. The durations of the classical "pinpoint" view, the pre- and post-event "intermediate" view, and the R-R interval plot are flexible and adjustable. In one embodiment, the diagnostic composite plot displays R-R interval data over a forty-minute duration and ECG data over short and medium durations (steps 34 and 35), such as four-second and 24-second durations that provide two- and 12-second segments of the ECG data before and after the R-R interval plot's temporal point of reference, which is generally in the center of the R-R interval plot, although other locations in the R-R interval plot could be identified as the temporal point of reference. The pinpoint "snapshot" and intermediate views of ECG data with the extended term R-R interval data comparatively depicts heart rate context and patterns of behavior prior to and after a clinically meaningful arrhythmia or patient concern, thereby enhancing diagnostic specificity of cardiac rhythm disorders and providing physiological context to improve diagnostic ability. In a further embodiment, diagnostically relevant cardiac events can be identified and the R-R interval plot can be constructed with a cardiac event centered in the middle (or other location) of the plot, which thereby allows pre- and post-event heart rhythm data to be contextually "framed" through the pinpoint and intermediate ECG data views. Other durations, intervals and presentations of ECG data are possible.

Figure 5:
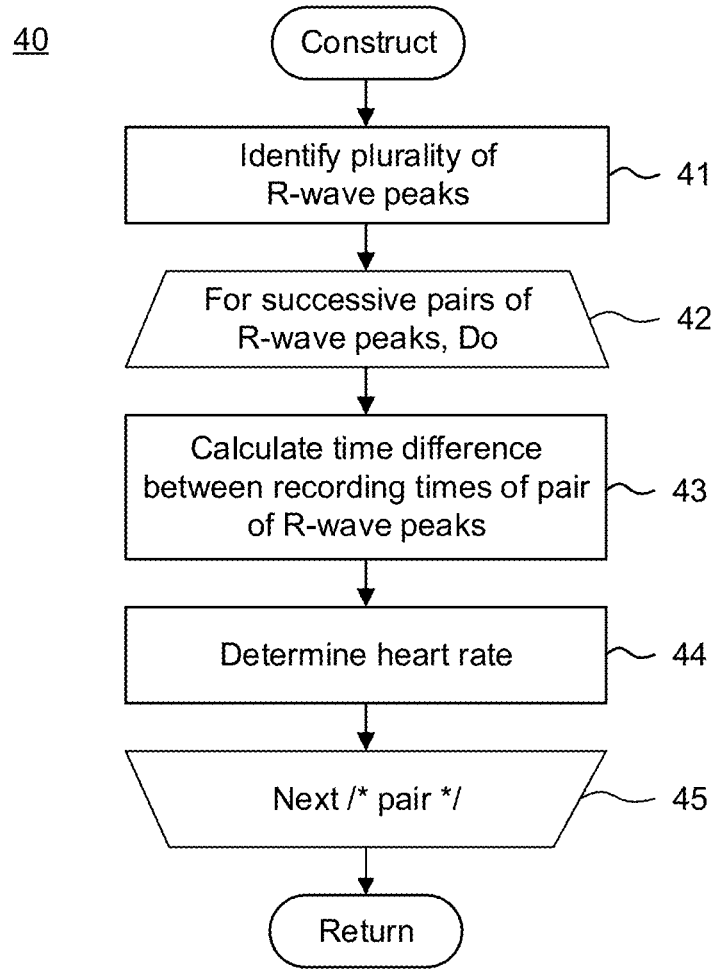
FIG. 5 is a flow diagram showing a routine for constructing an extended-duration R-R interval plot for use in the routine of FIG. 4.

The extended-duration R-R interval plot presents beat-to-beat heart rate variability in a format that is intuitive and contextual, yet condensed. The format of the R-R interval plot is selected to optimize visualization of cardiac events in a compressed, yet understandable field of view, that allows for compact presentation of the data akin to a cardiologists understanding of clinical events. FIG. 5 is a flow diagram showing a routine 40 for constructing an extended-duration R-R interval plot for use in the routine 30 of FIG. 4. The duration of the R-R interval plot can vary from less than one minute to the entire duration of the recording. Thus, a plurality of R-wave peaks is first selected out of the vector of ECG data (step 41) appropriate to the duration of the R-R interval plot to be constructed. For successive pairs of the R-wave peaks (steps 42-43), the difference between the recording times of the R-peaks is calculated (step 43). Each recording time difference represents the length of one heartbeat. The heart rate associated with the recording time difference is determined by taking an inverse of the recording time difference and normalizing the inverse to beats per minute (step 44). Taking the inverse of the recording time difference yields a heart rate expressed in beats per second, which can be adjusted by a factor of 60 to provide a heart rate expressed in bpm. Calculation of the differences between the recording times and the associated heart rate continues for all of the remaining pairs of the R-wave peaks (step 44).

The pairings of R-R intervals and associated heart rates are formed into a two-dimensional plot. R-R intervals are plotted along the x-axis and associated heart rates are plotted along the y-axis. The range and scale of the y-axis (heart rate) can be adjusted according to the range and frequency of normal or patient-specific heart rates, so as to increase the visual distinctions between the heart rates that correspond to different R-R intervals. In one embodiment, the y-axis of the R-R interval plot has a range of 20 to 300 beats per minute and R-R intervals corresponding to heart rates falling extremely outside of this range are excluded to allow easy visualization of 99+% of the heart rate possibilities.

In a further embodiment, the y-axis has a non-linear scale that is calculated as a function of the x-axis (R-R interval), such that:

$$y = \left(\frac{x - \min bpm}{\max bpm - \min bpm}\right)^n$$

where x is the time difference, min bpm is the minimum heart rate, max bpm is the maximum heart rate, and n<1. The non-linear scale of the y-axis accentuates the spatial distance between successive heart rates when heart rate is low. For example, when n=2, the spatial difference between 50 and 60 bpm is 32% larger than the spatial difference between 90 bpm and 100 bpm, and 68% larger than the spatial difference between 150 bpm and 160 bpm. As a result the overall effect is to accentuate the spatial differences in frequently-occurring ranges of heart rate and de-emphasize the spatial differential in ranges of heart rate where a deviation from norm would have been apparent, thus maximizing the spatial efficiency in data presentation. The goal is to show cardiac events in a simple, small visual contextual format. Larger scales and larger formats bely the practical limits of single-page presentations for the easy visualization at a glance by the busy physician. The visual distinctions between the heart rates that correspond to different R-R intervals stand out, especially when plotted on a non-linear scale. Other y-axis ranges and scales are possible as may be selected by distinct clinical needs and specific diagnostic requirements.

Figure 6:
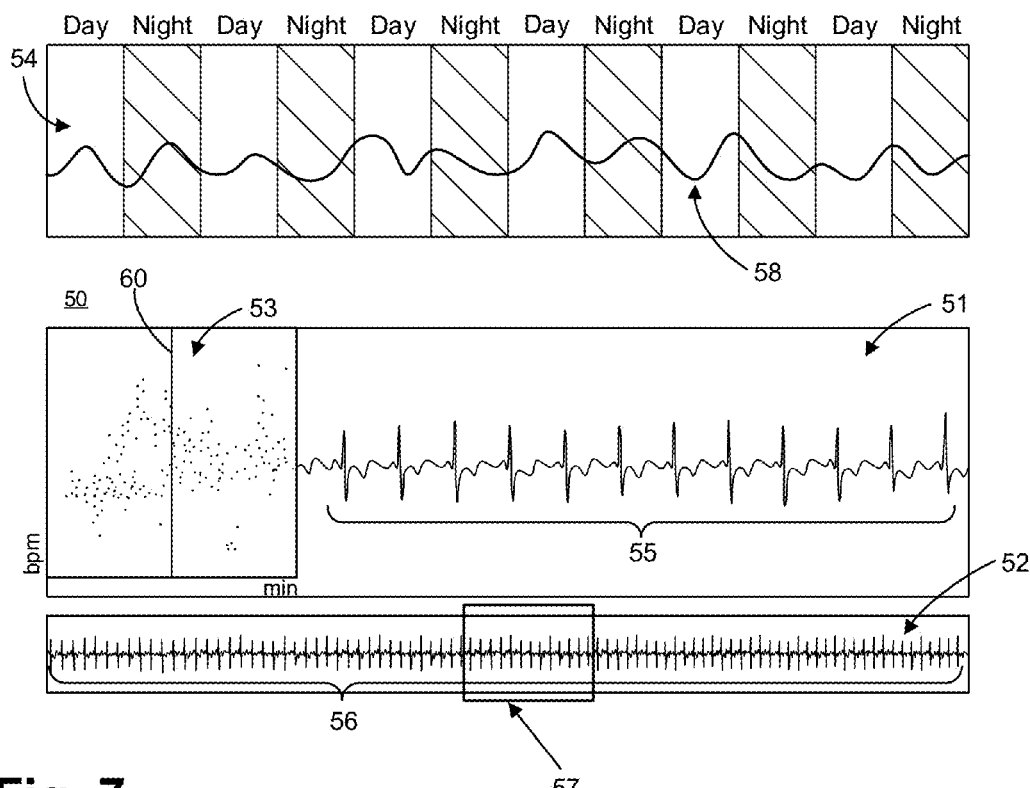
FIG. 6 is a diagram showing, by way of example, a diagnostic composite plot generated by the method of FIG. 3.

The diagnostic composite plot includes a single, long range view of R-R interval data and a pair of pinpoint ECG data views that together help to facilitate rhythm disorder diagnosis by placing focused long-term heart rate information alongside short-term and medium-term ECG information. Such pairing of ECG and R-R interval data is unique in its ability to inform the physician of events prior to, during and after a cardiovascular event. FIG. 6 is a diagram showing, by way of example, a diagnostic composite plot 50 generated by the method 30 of FIG. 3. Note that the diagnostic composite plot can be tailored to include more than one view of R-R interval data and as many views of contextual ECG data as needed. In a further embodiment, a background information plot presenting an extended far field of related information can be included, such as activity amount, activity intensity, posture, syncope impulse detection, respiratory rate, blood pressure, oxygen saturation ($SpO_2$), blood carbon dioxide level ($pCO_2$), glucose, lung wetness, and temperature. Other forms of background information are possible. In a still further embodiment, background information can be layered on top of or keyed to the diagnostic composite plot 50, particularly at key points of time in the R-R interval data plot, so that the context provided by each item of background information can be readily accessed by the reviewing physician.

The diagnostic composite plot 50 includes an ECG plot presenting a near field (short duration) view 51, an ECG plot presenting an intermediate field (medium duration) view 52, and an R-R interval data plot presenting a far field (extended duration) view 53. The three views 51, 52, 53 are juxtaposed alongside one other to allow quick back and forth referencing of the full context of the heart's normal and abnormal physiology. Typically, a temporal point of reference, which could be a diagnostically relevant cardiac event, patient concern or other indicia, would be identified and centered on the x-axis in all three views. The placement of the temporal point of reference in the middle of all three x-axes enables the ECG data to be temporally keyed to the R-R interval data appearing in the center 60 of the R-R interval data view 53, with a near field view 51 of an ECG displayed at normal (paper-based) recording speed and a intermediate field view 52 that presents the ECG data occurring before and after the center 60. As a result, the near field view 51 provides the ECG data corresponding to the R-R interval data at the center 60 (or other location) in a format that is familiar to all physicians, while the intermediate field view 52 enables presentation of the broader ECG data context going beyond the borders of the near field view 51. In a further embodiment, the center 60 can be slidably adjusted backwards and forwards in time, with the near field view 51 and the far field view 52 of the ECG data automatically adjusting accordingly to stay in context with the R-R interval data view 51. In a still further embodiment, multiple temporal points of reference can be identified with each temporal point of reference being optionally accompanied by one or more dedicated sets of ECG data views.

The collection of plots are conveniently arranged close enough to one another to facilitate printing on a single page of standard sized paper (or physical paper substitute, such as a PDF file), although other layouts of the plots are possible. The far field view 53 is plotted with time in the x-axis and heart rate in the y-axis. The R-R intervals are calculated by measuring the time occurring between successive R-wave peaks. In one embodiment, the far field view 53 presents R-R interval data (expressed as heart rate in bpm) that begins about 20 minutes prior to and ends about 20 minutes following the center 60, although other durations are possible.

The near field view 51 and intermediate field view 52 present ECG data relative to the center 60 of the far field view 53. The near field view 51 provides a pinpoint or short duration view of the ECG data. In one embodiment, the near field view 51 presents ECG data 55 that begins about two seconds prior to and ends about two seconds following the center 60, although other durations are possible. The intermediate field view 52 provides additional contextual ECG information allowing the physician to assess the ECG itself and gather a broader view of the rhythm before and after a "blow-up" of the specific arrhythmia of interest. In one embodiment, the intermediate field view 52 presents ECG data 56 that begins about 12 seconds prior to and ends about 12 seconds following the center 60, although other durations are possible. For convenience, the eight-second interval of the ECG data 56 in the intermediate field view 52 that makes up the ECG data 56 in the near field view 51 is visually highlighted, here, with a surrounding box 57. In addition, other views of the ECG data, either in addition to or in lieu of the near field view 51 and the far field view 52 are possible. Optionally, an ECG plot presenting an extended far field view 54 of the background information can be included in the diagnostic composite plot 50. In one embodiment, the background information is presented as average heart rate with day and night periods 58 alternately shaded along the x-axis. Other types of background information, such as activity amount, activity intensity, posture, syncope impulse detection, respiratory rate, blood pressure, oxygen saturation ($SpO_2$), blood carbon dioxide level ($pCO_2$), glucose, lung wetness, and temperature, are possible.

Figure 7:
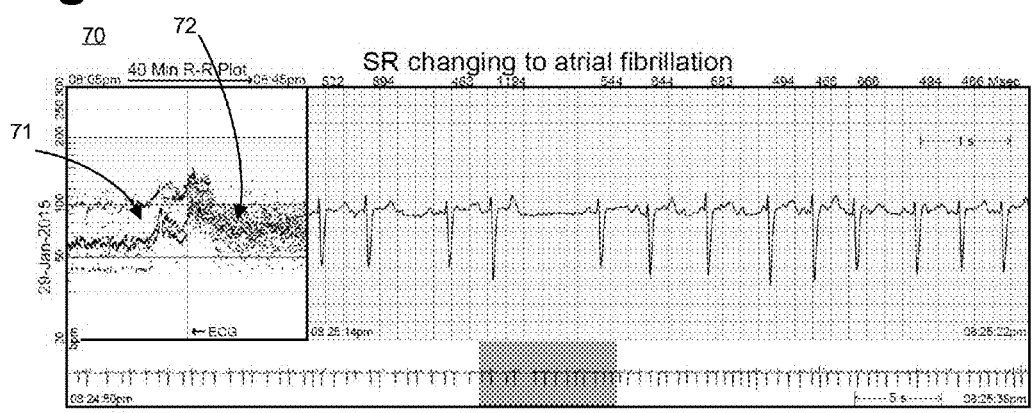
FIG. 7 is a diagram showing, by way of example, a diagnostic composite plot for facilitating the diagnosis of sinus rhythm (SR) transitioning into atrial fibrillation (AF).

Examples of the diagnostic composite plot as applied to specific forms of cardiac rhythm disorders will now be discussed. These examples help to illustrate the distinctive weightings that accompany different forms of rhythm disorders and the R-R interval and ECG waveform deflection context with which they occur. FIG. 7 is a diagram showing, by way of example, a diagnostic composite plot 70 for facilitating the diagnosis of sinus rhythm (SR) transitioning into AF. SR is indicated through the presence of a reasonably steady baseline, but with subsidiary lines of premature beats and their compensatory pauses. SR manifests as a shadowing 71 of a high heart rate line and a low heart rate line. AF is characterized by irregular heartbeats with a somewhat random variation of R-R intervals, although within a limited range and concentrating in a Gaussian-like distribution pattern around a mean that varies over time. Although AF can be diagnosed by viewing a near field view 51 of ECG data showing heartbeats with reversed P-wave and irregular R-R intervals, this approach may be unclear when viewing "snippets" of ECG data, especially when associated with poor quality ECG signals. The presence of AF can also be confirmed through a far field view 53 of R-R interval data, in which the R-R intervals assume superficially appearing disorganized, spread-out and decentralized scattered cloud 72 along the x-axis, in comparison to a concentrated, darkened line typical of a more organized cardiac rhythm.

Figure 8:
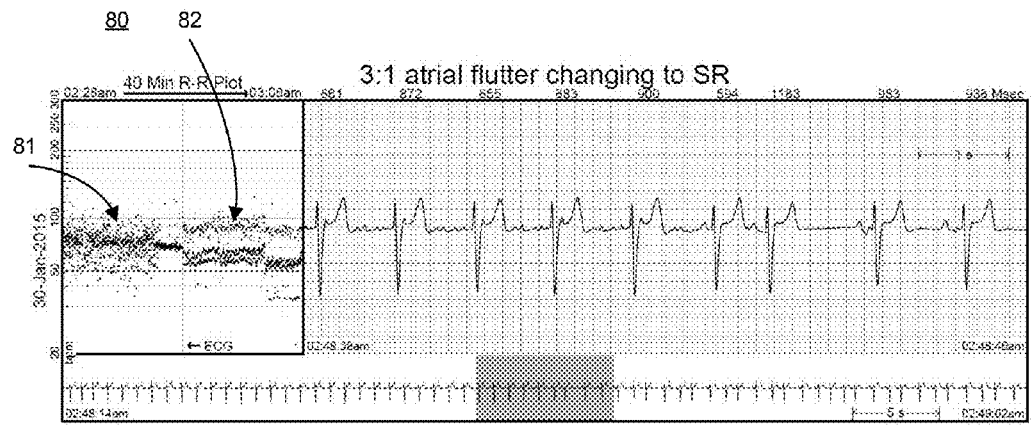
FIG. 8 is a diagram showing, by way of example, a diagnostic composite plot for facilitating the diagnosis of 3:1 atrial flutter (AFL) transitioning into SR.

FIG. 8 is a diagram showing, by way of example, a diagnostic composite plot 80 for facilitating the diagnosis of 3:1 atrial flutter (AFL) transitioning into SR with frequent premature ectopic atrial beats. In the initial part of the R-R interval plot, the R-R intervals have a discernible aggregated line in the middle of the cloud 81 when the rhythm has yet to stabilize into a set pattern, not quite AF and not quite AFL. Immediately thereafter, a dense line representing firm 3:1 atrial flutter stabilizes the rhythm prior to the transition into SR associated with the presence of two seesawing baselines that result from frequent atrial ectopy causing short coupling intervals and then compensatory long coupling intervals. SR is indicated by the middle of the three lines with a low heart rate line consistent with the compensatory pause (long coupling interval) and a high heart rate line with the shortest coupling interval representing the series of atrial premature beats 82, and thus, at a faster heart rate.

Figure 9:
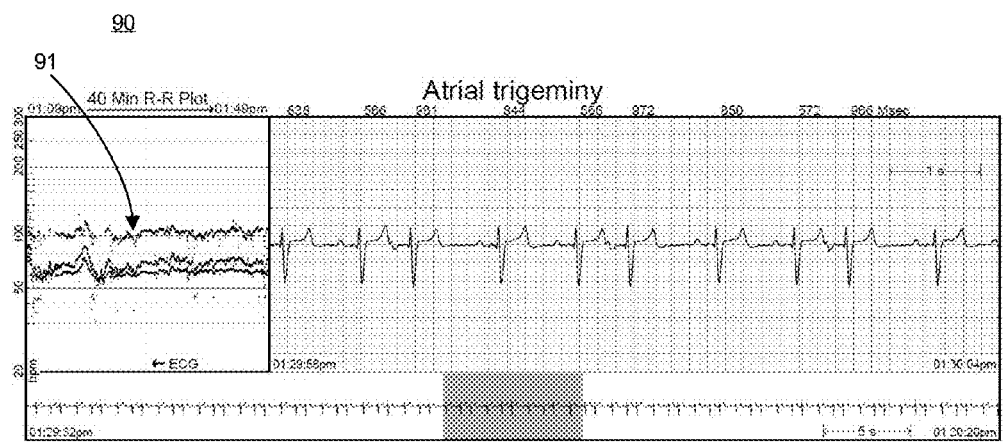
FIG. 9 is a diagram showing, by way of example, a diagnostic composite plot for facilitating the diagnosis of atrial trigeminy.

FIG. 9 is a diagram showing, by way of example, a diagnostic composite plot 90 for facilitating the diagnosis of atrial trigeminy. Atrial trigeminy is characterized by three heartbeat rates appearing intermittently yet reasonably regularly. Although atrial trigeminy can be diagnosed by viewing a near field view 51 of ECG data, the pattern is significantly more recognizable in a far field view 53 of R-R interval data, in which a repeating pattern of three distinct heartbeat lines are persistently present and clearly visible 91. This view also provides the physician with a qualitative feel for the frequency of the event troubling the patient that is not discernible from a single ECG strip.

Figure 10:
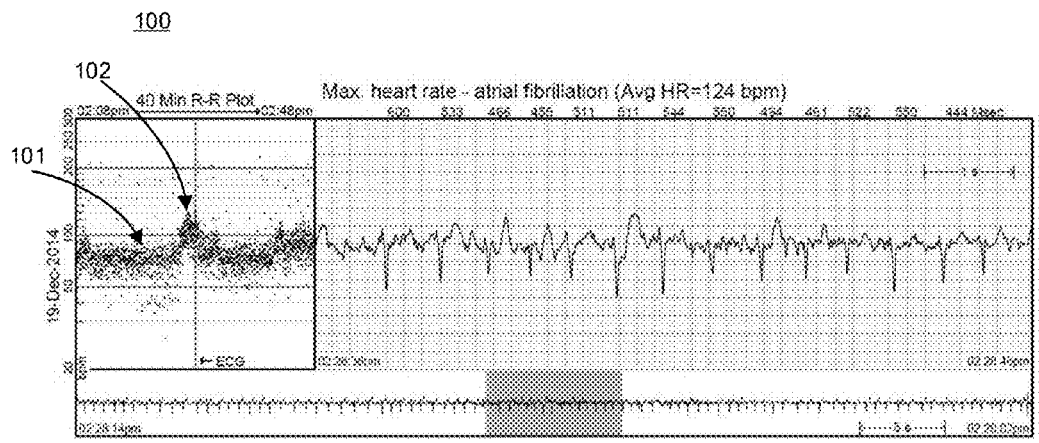
FIG. 10 is a diagram showing, by way of example, a diagnostic composite plot for facilitating the diagnosis of maximum heart rate in an episode of AF during exercise.

FIG. 10 is a diagram showing, by way of example, a diagnostic composite plot 100 for facilitating the diagnosis of maximum heart rate in an episode of AF during exercise. In a far field view 50 of R-R interval data, AF manifests through a dispersed cloud of dots (Gaussian-like distribution) without a discernible main heart rate line representing regular heartbeats 101. Under exercise, the maximum heartbeat can be located by an increase in heart rate clustered about the cloud 102. In addition, individual dots above the 200 bpm range throughout the entire 40-minute range indicates the maximum heart rate during exercise. The very rapid rise in heart rate can be critical to patient management, as such bumps in rate by exercise can prove serious and even trigger cardiac arrest. Their very presence is easily visualized in the R-R interval data plot, thereby allowing the physician to alter therapy sufficiently to control such potentially damaging rises in heart rate.

Figure 11:
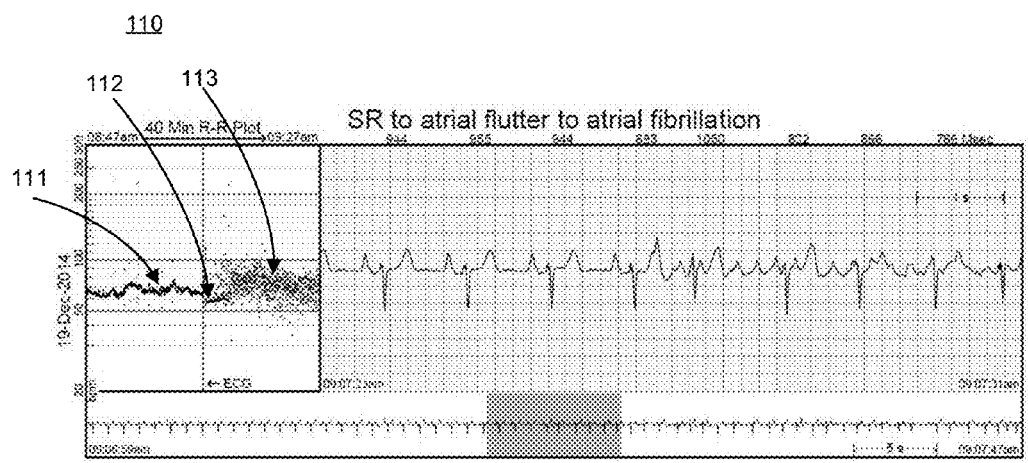
FIG. 11 is a diagram showing, by way of example, a diagnostic composite plot for facilitating the diagnosis of SR transitioning into AFL transitioning into AF.

FIG. 11 is a diagram showing, by way of example, a diagnostic composite plot 110 for facilitating the diagnosis of SR transitioning into AFL transitioning into AF. In a far field view 53 of R-R interval data, SR manifests as an uneven main heart rate line with a fluctuating height 111. At the onset of AFL, the main heart rate line breaks away at a lower heart rate than the SR main heart rate line 112. The episode of AFL further evolves into AF as characterized by a dispersed cloud of irregular heartbeats without concentrated heart rate lines 113. This view provides critical information to the physician managing AF patients in that, at a glance, the view provides data that tells the physician that the patient's AF may be the consequence of AFL. Such knowledge may alter both drug and procedure therapies, like catheter ablation details of intervention.

Figure 12:
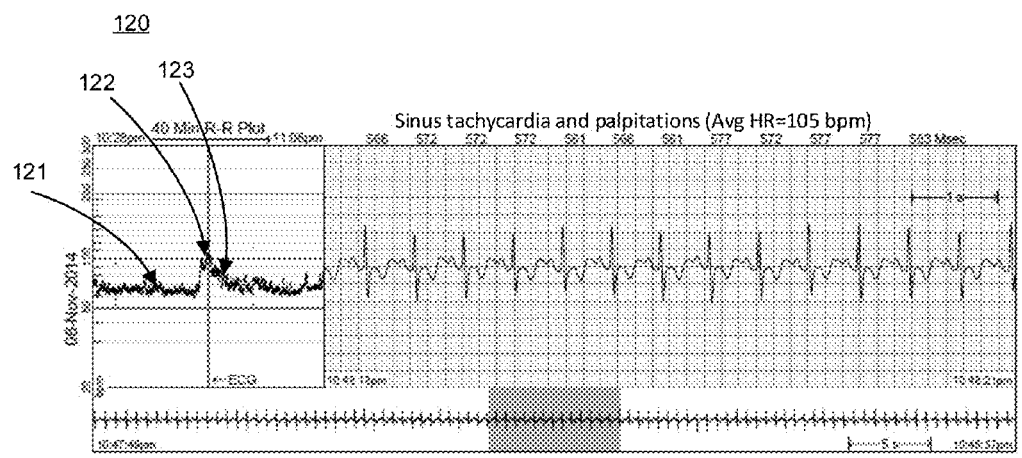
FIG. 12 is a diagram showing, by way of example, a diagnostic composite plot for facilitating the diagnosis of sinus tachycardia and palpitations that occurred during exercise accompanied by a jump in heart rate.

FIG. 12 is a diagram showing, by way of example, a diagnostic composite plot 120 for facilitating the diagnosis of sinus tachycardia and palpitations that occurred during exercise accompanied by a jump in heart rate. In a far field view 50 of R-R interval data, sinus tachycardia is indicated by the presence of a baseline heart rate of about 60 bpm 121 that spikes up to around 100 bpm 122 and gradually slopes down with a wide tail 123, reflecting a sharp rise of heart rates followed by a gradual decline. The associated ECG data in the near field and intermediate field views (not shown) can confirm the rhythm as sinus rhythm and a normal response to exercise. This rhythm, although superficially obvious, was associated with symptoms of palpitations and demonstrates a sensitivity to heart rate fluctuations, rather than a sensitivity to an arrhythmia. This common problem is often dismissed as merely sinus tachycardia, rather than recognizing the context of a changing rate that generated the patient's complaint, a problem, visible only in the R-R interval data plot.

Figure 13:
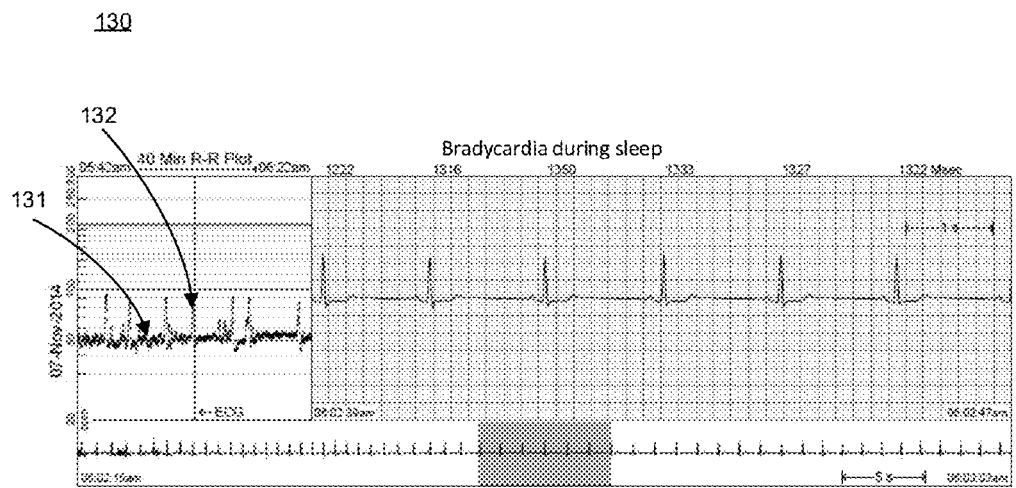
FIG. 13 is a diagram showing, by way of example, a diagnostic composite plot for facilitating the diagnosis of bradycardia.

FIG. 13 is a diagram showing, by way of example, a diagnostic composite plot 90 for facilitating the diagnosis of bradycardia during sleep and a R-R interval pattern characteristic of sleep. Bradycardia refers to a resting heart rate of under 60 bpm. Bradycardia during sleep is often tempered with occasional spikes of rapid heart rate, which can be a secondary compensatory response to dreaming, snoring or sleep apnea. In a far field view 50 of R-R interval data, bradycardia manifests as the presence of a base line heart rate in the range of about 50 bpm 131, coupled with multiple spikes of dots 132 representing intermittent episodes of elevated heart rate. Such elevations in heart rate during a pre-dominantly slower rate may be signs of a cardio-respiratory disorder. Still other applications of the diagnostic composite plot 80 are possible.

The diagnostic composite plots are a tool used by physicians as part of a continuum of cardiac care provisioning that begins with ECG monitoring, continues through diagnostic overread and finally, if medically appropriate, concludes with cardiac rhythm disorder treatment. Each of these steps involve different physical components that collaboratively allow physicians to acquire and visualize R-R interval and ECG data in a way that accurately depicts heart rate variability over time. FIG. 14 is a block diagram showing a system 140 for facilitating diagnosis of cardiac rhythm disorders with the aid of a digital computer 150 in accordance with one embodiment. Each diagnostic composite plot 151 is based on ECG data 166 that has either been recorded by a conventional electrocardiograph (not shown) or retrieved or obtained from some other type of ECG monitoring and recording device. Following completion of the ECG monitoring, the ECG data is assembled into a diagnostic composite plot 151, which can be used by a physician to diagnosis and, if required, treat a cardiac rhythm disorder, or for other health care or related purposes.

Each diagnostic composite plot 151 is based on ECG data 166 that has been recorded over a period of observation, which can be for just a short term, such as during a clinic appointment, or over an extended time frame of months. ECG recordation and, in some cases, physiological monitoring can be provided through various types of ECG-capable monitoring ensembles, including a standardized 12-lead ECG setup (not shown), such as used for clinical ECG monitoring, a portable Holter-type ECG recorder for traditional ambulatory ECG monitoring (also not shown), or a wearable ambulatory ECG monitor.

One form of ambulatory ECG monitor 142 particularly suited to monitoring and recording ECG and physiological data employs an electrode patch 143 and a removable reusable (or single use) monitor recorder 144, such as described in commonly-assigned U.S. patent application Ser. No. 14/997,416, cited supra. The electrode patch 143 and monitor recorder 144 are synergistically optimized to capture electrical signals from the propagation of low amplitude, relatively low frequency content cardiac action potentials, particularly the P-waves generated during atrial activation. The ECG monitor 142 sits centrally (in the midline) on the patient's chest along the sternum 169 oriented top-to-bottom. The ECG monitor 142 interfaces to a pair of cutaneous electrodes (not shown) on the electrode patch 143 that are adhered to the patient's skin along the sternal midline (or immediately to either side of the sternum 169). The ECG monitor 142 has a unique narrow "hourglass"-like shape that significantly improves the ability of the monitor to be comfortably worn by the patient 141 for an extended period of time and to cutaneously sense cardiac electric signals, particularly the P-wave (or atrial activity) and, to a lesser extent, the QRS interval signals in the ECG waveforms indicating ventricular activity.

The electrode patch 143 itself is shaped to conform to the contours of the patient's chest approximately centered on the sternal midline. To counter the dislodgment due to compressional and torsional forces, a layer of non-irritating adhesive, such as hydrocolloid, is provided at least partially on the underside, or contact, surface of the electrode patch, but only on the electrode patch's distal and proximal ends. To counter dislodgment due to tensile and torsional forces, a strain relief is defined in the electrode patch's flexible circuit using cut-outs partially extending transversely from each opposite side of the flexible circuit and continuing longitudinally towards each other to define in 'S'-shaped pattern. In a further embodiment, the electrode patch 143 is made from a type of stretchable spunlace fabric. To counter patient bending motions and prevent disadhesion of the electrode patch 143, the outward-facing aspect of the backing, to which a (non-stretchable) flexible circuit is fixedly attached, stretches at a different rate than the backing's skin-facing aspect, where a skin adhesive removably affixes the electrode patch 143 to the skin. Each of these components are distinctive and allow for comfortable and extended wear, especially by women, where breast mobility would otherwise interfere with ECG monitor use and comfort. Still other forms of ECG monitoring and recording assembles are possible.

When operated standalone, the monitor recorder 142 senses and records the patient's ECG data 166 and physiological data (not shown) into a memory onboard the monitor recorder 144. The recorded data can be downloaded using a download station 147, which could be a dedicated download station 145 that permits the retrieval of stored ECG data 166 and physiological data, if applicable, execution of diagnostics on or programming of the monitor recorder 144, or performance of other functions. To facilitate physical connection with the download station 145, the monitor recorder 144 has a set of electrical contacts (not shown) that enable the monitor recorder 144 to physically interface to a set of terminals 148. In turn, the download station 145 can be operated through user controls 149 to execute a communications or data download program 146 ("Download") or similar program that interacts with the monitor recorder 144 via the physical interface to retrieve the stored ECG data 166. The download station 145 could alternatively be a server, personal computer, tablet or handheld computer, smart mobile device, or purpose-built device designed specific to the task of interfacing with a monitor recorder 144. Still other forms of download station 145 are possible. In a further embodiment, the ECG data 166 from the monitor recorder 144 can be offloaded wirelessly.

The ECG data 166 can be retrieved from the download station 145 using a control program 157 ("Ctl") or analogous application executing on a personal digital computer 156 or other connectable computing device, via a hard wired link 158, wireless link (not shown), or by physical transfer of storage media (not shown). The personal digital computer 156 may also execute middleware (not shown) that converts the ECG data 166 into a format suitable for use by a third-party post-monitoring analysis program. The personal digital computer 156 stores the ECG data 166 along with each patient's electronic medical records (EMRs) 165 in the secure database 64, as further discussed infra. In a further embodiment, the download station 145 is able to directly interface with other devices over a computer communications network 155, which could be a combination of local area and wide area networks, including the Internet or another telecommunications network, over wired or wireless connections.

A client-server model can be employed for ECG data 166 analysis. In this model, a server 62 executes a patient management program 160 ("Mgt") or similar application that accesses the retrieved ECG data 166 and other information in the secure database 164 cataloged with each patient's EMRs 165. The patients' EMRs can be supplemented with other information (not shown), such as medical history, testing results, and so forth, which can be factored into automated diagnosis and treatment. The patient management program 160, or other trusted application, also maintains and safeguards the secure database 164 to limit access to patient EMRs 165 to only authorized parties for appropriate medical or other uses, such as mandated by state or federal law, such as under the Health Insurance Portability and Accountability Act (HIPAA) or per the European Union's Data Protection Directive. Other schemes and safeguards to protect and maintain the integrity of patient EMRs 165 are possible.

In a further embodiment, the wearable monitor 142 can interoperate wirelessly with other wearable or implantable physiology monitors and activity sensors 152, such as activity trackers worn on the wrist or body, and with mobile devices 153, including smart watches and smartphones. Wearable or implantable physiology monitors and activity sensors 152 encompass a wide range of wirelessly interconnectable devices that measure or monitor a patient's physiological data, such as heart rate, temperature, blood pressure, respiratory rate, blood pressure, blood sugar (with or without an appropriate subcutaneous probe), oxygen saturation, minute ventilation, and so on; physical states, such as movement, sleep, footsteps, and the like; and performance, including calories burned or estimated blood glucose level. Frequently, wearable and implantable physiology monitors and activity sensors 152 are capable of wirelessly interfacing with mobile devices 153, particularly smart mobile devices, including so-called "smartphones" and "smart watches," as well as with personal computers and tablet or handheld computers, to download monitoring data either in real-time or in batches through an application ("App") or similar program.

Based on the ECG data 166, physicians can rely on the data as medically certifiable and are able to directly proceed with diagnosing cardiac rhythm disorders and determining the appropriate course of treatment for the patient 141, including undertaking further medical interventions as appropriate. The ECG data 166 can be retrieved by a digital computer 150 over the network 155. A diagnostic composite plot 151 that includes multiple temporal points of reference and a plot of R-R interval data is then constructed based on the ECG data 166, as discussed in detail supra with reference to FIG. 3, and displayed or, alternatively, printed, for use by a physician.

In a further embodiment, the server 159 executes a patient diagnosis program 161 ("Dx") or similar application that can evaluate the ECG data 166 to form a diagnosis of a cardiac rhythm disorder. The patient diagnosis program 161 compares and evaluates the ECG data 166 to a set of medical diagnostic criteria 167, from which a diagnostic overread 162 ("diagnosis") is generated. Each diagnostic overread 162 can include one or more diagnostic findings 168 that can be rated by degree of severity, such as with the automated diagnosis of atrial fibrillation. If at least one of the diagnostic findings 168 for a patient exceed a threshold level of tolerance, which may be tailored to a specific client, disease or medical condition group, or applied to a general patient population, in a still further embodiment, therapeutic treatment ("Therapy") to address diagnosed disorder findings can be generated and, optionally, programmed into a cardiac rhythm therapy delivery device, such as an IMD (not shown), including a pacemaker, implantable cardioverter defibrillator (ICD), or similar devices.

While the invention has been particularly shown and described as referenced to the embodiments thereof, those skilled in the art will understand that the foregoing and other changes in form and detail may be made therein without departing from the spirit and scope.

What is claimed is:

1. A system for facilitating diagnosis of cardiac rhythm disorders with the aid of a digital computer, comprising:
   an electrocardiogram (ECG) monitoring and recording device;
   a download station adapted to retrieve cutaneous action potentials recorded for a set time period by the ECG monitoring and recording device as ECG data;
   a processor and memory within which code for execution by the processor is stored, further comprising:
      an identification module configured to identify a plurality of R-wave peaks in the ECG data;
      a calculation module configured to calculate a difference between recording times of successive pairs of the R-wave peaks and to determine a heart rate associated with each time difference; and
      a construction module configured to form an extended duration R-R interval plot over the set time period comprising each of the recording time differences and the associated heart rates; and
   a display operatively coupled to the processor, for displaying:
      the extended duration R-R interval plot with a temporal point of reference in the extended duration R-R interval plot; and
      at least one accompanying ECG plot comprising at least part of the ECG data preceding and following the temporal point of reference as context.

2. A system in accordance with claim 1, further comprising at least one of:
   the at least one accompanying ECG plot adapted to be presented as a ECG view produced at a traditional paper-based ECG recording speed; and
   the at least one accompanying ECG plot adapted to be presented as a lower resolution, pre- and post-event contextual view relative to the temporal point of reference.

3. A system in accordance with claim 1, further comprising at least one of:
   the construction module further configured to limit the heart rates to a range outside of which the time differences and the associated heart rates are excluded from the extended duration R-R interval plot; and
   the construction module further configured to construct the extended duration R-R interval plot with a non-linear scale for the heart rates.

4. A system in accordance with claim 3, wherein the non-linear scale for the heart rates is determined in accordance with the equation:

$$y = \left( \frac{x - \min bpm}{\max bpm - \min bpm} \right)^n$$

where x is the time difference, min bpm is the minimum heart rate (in beats per minute), max bpm is the maximum heart rate, and n<1.

5. A system in accordance with claim 1, further comprising:
   an ambulatory ECG monitor disposed for wear on the patient's chest along the sternum and adapted to record the cutaneous action potentials, the ambulatory ECG monitor adapted to be interfaced to a pair of cutaneous electrodes adhered to the patient's skin along the sternal midline.

6. A system in accordance with claim 1, the processor further comprising:
   an identification module configured to identify a potentially-actionable cardiac event within the ECG data, and to select the plurality of R-wave peaks from the ECG data prior to and after the potentially-actionable cardiac event.

7. A system in accordance with claim 1, the processor further comprising:
   a diagnostic module configured to form a diagnosis based on heart rate variability patterns in the extended duration R-R interval plot.

8. A system in accordance with claim 7, further comprising:
   the diagnostic module further configured to detect atrial fibrillation by identifying a Gaussian-type distribution of heart rate variability in the extended duration R-R interval plot.

9. A system in accordance with claim 7, further comprising:
   a cardiac rhythm therapy delivery device programmed to deliver a therapy in response to the diagnosis.

10. A system in accordance with claim 1, wherein the processor is configured to form:
- a background information plot with the extended duration R-R interval plot comprising one or more of activity amount, activity intensity, posture, syncope impulse detection, respiratory rate, blood pressure, oxygen saturation ($SpO_2$), blood carbon dioxide level ($pCO_2$), glucose, lung wetness, and temperature; and
- background information layered to or keyed with the extended duration R-R interval plot comprising one or more of activity amount, activity intensity, posture, syncope impulse detection, respiratory rate, blood pressure, oxygen saturation ($SpO_2$), blood carbon dioxide level ($pCO_2$), glucose, lung wetness, and temperature.

11. A method for facilitating diagnosis of cardiac rhythm disorders with the aid of a digital computer, comprising the steps of:
- monitoring and recording cutaneous action potentials of a patient;
- retrieving the cutaneous action potentials as electrocardiogram (ECG) data for a set time period and identifying a plurality of R-wave peaks in the ECG data;
- calculating a difference between recording times of successive pairs of the R-wave peaks and determining a heart rate associated with each time difference;
- forming an extended duration R-R interval plot over the set time period comprising each of the recording time differences and the associated heart rates;
- displaying the extended duration R-R interval plot and identifying a temporal point of reference in the extended duration R-R interval plot; and
- displaying at least part of the ECG data preceding and following the temporal point of reference as context in at least one accompanying ECG plot.

12. A method in accordance with claim 11, further comprising at least one of the steps of:
- presenting the at least one accompanying ECG plot as a ECG view produced at a traditional paper-based ECG recording speed; and
- presenting the at least one accompanying ECG plot as a lower resolution, pre- and post-event contextual view relative to the temporal point of reference.

13. A method in accordance with claim 11, further comprising at least one of the steps of:
- limiting the heart rates to a range outside of which the time differences and the associated heart rates are excluded from the extended duration R-R interval plot; and
- constructing the extended duration R-R interval plot with a non-linear scale for the heart rates.

14. A method in accordance with claim 13, wherein the non-linear scale for the heart rates is determined in accordance with the equation:

$$y = \left( \frac{x - \min bpm}{\max bpm - \min bpm} \right)^n$$

where x is the time difference, min bpm is the minimum heart rate (in beats per minute), max bpm is the maximum heart rate, and n<1.

15. A method in accordance with claim 11, further comprising the step of:
- recording the cutaneous action potentials through an ambulatory ECG monitor disposed for wear on the patient's chest along the sternum, the ambulatory ECG monitor adapted to be interfaced to a pair of cutaneous electrodes adhered to the patient's skin along the sternal midline.

16. A method in accordance with claim 11, further comprising the steps of:
- identifying a potentially-actionable cardiac event within the ECG data; and
- selecting the plurality of R-wave peaks from the ECG data prior to and after the potentially-actionable cardiac event.

17. A method in accordance with claim 11, further comprising the step of:
- forming a diagnosis based on heart rate variability patterns identified in the extended duration R-R interval plot.

18. A method in accordance with claim 17, further comprising the steps of:
- detecting atrial fibrillation by identifying a Gaussian-type distribution of heart rate variability in the extended duration R-R interval plot.

19. A method in accordance with claim 18, further comprising the step of:
- programming a therapy in response to the diagnosis into a cardiac rhythm therapy delivery device.

20. A method in accordance with claim 11, further comprising at least one of the steps of:
- including a background information plot with the extended duration R-R interval plot comprising one or more of activity amount, activity intensity, posture, syncope impulse detection, respiratory rate, blood pressure, oxygen saturation ($SpO_2$), blood carbon dioxide level ($pCO_2$), glucose, lung wetness, and temperature; and
- layering or keying background information with the extended duration R-R interval plot comprising one or more of activity amount, activity intensity, posture, syncope impulse detection, respiratory rate, blood pressure, oxygen saturation ($SpO_2$), blood carbon dioxide level ($pCO_2$), glucose, lung wetness, and temperature.

21. A non-transitory computer readable storage medium storing code for executing on a computer system to perform the method according to claim 11.

* * * * *